(12) United States Patent
Ibrahim et al.

(10) Patent No.: US 12,116,365 B2
(45) Date of Patent: *Oct. 15, 2024

(54) HETEROCYCLIC COMPOUNDS AND USES THEREOF

(71) Applicant: Opna Bio SA, Epalinges (CH)

(72) Inventors: Prabha N. Ibrahim, Mountain View, CA (US); Wayne Spevak, Berkeley, CA (US); Jiazhong Zhang, Foster City, CA (US); Songyuan Shi, Fremont, CA (US); Ben Powell, Pleasant Hill, CA (US); Yan Ma, Belmont, CA (US)

(73) Assignee: OPNA BIO SA, Epalinges (CH)

( * ) Notice: Subject to any disclaimer, the term of this patent is extended or adjusted under 35 U.S.C. 154(b) by 129 days.

This patent is subject to a terminal disclaimer.

(21) Appl. No.: 17/690,892

(22) Filed: Mar. 9, 2022

(65) Prior Publication Data

US 2022/0356183 A1   Nov. 10, 2022

Related U.S. Application Data

(63) Continuation of application No. 17/387,775, filed on Jul. 28, 2021, now abandoned, which is a continuation of application No. 17/121,484, filed on Dec. 14, 2020, now abandoned, which is a continuation of application No. 16/838,383, filed on Apr. 2, 2020, now Pat. No. 10,899,761, which is a continuation of application No. 16/441,610, filed on Jun. 14, 2019, now Pat. No. 10,647,716, which is a continuation of application No. 15/977,772, filed on May 11, 2018, now Pat. No. 10,370,374, which is a continuation of application No. 15/689,931, filed on Aug. 29, 2017, now Pat. No. 9,975,894, which is a continuation of application No. 15/269,054, filed on Sep. 19, 2016, now Pat. No. 9,771,363.

(60) Provisional application No. 62/221,508, filed on Sep. 21, 2015.

(51) Int. Cl.
*C07D 471/04* (2006.01)
*A61K 31/437* (2006.01)
*A61K 31/444* (2006.01)
*A61K 31/5377* (2006.01)

(52) U.S. Cl.
CPC .......... *C07D 471/04* (2013.01); *A61K 31/444* (2013.01); *A61K 31/5377* (2013.01)

(58) Field of Classification Search
CPC ...... C07D 471/04; A61P 35/00; A61K 31/437
USPC .......................................... 546/113; 514/300
See application file for complete search history.

(56) References Cited

U.S. PATENT DOCUMENTS 9,771,363 B2 * 9/2017 Ibrahim .................. A61P 19/08
9,975,894 B2 * 5/2018 Ibrahim .................. A61P 11/02
2014/0303121 A1   10/2014 Zhang et al.

FOREIGN PATENT DOCUMENTS

| | | |
|---|---|---|
| JP | 2014509316 A | 4/2014 |
| JP | 2015526441 A | 9/2015 |
| JP | 2015526442 A | 9/2015 |
| WO | 2014145051 A1 | 9/2014 |
| WO | 2014182929 A1 | 11/2014 |

* cited by examiner

*Primary Examiner* — Charanjit Aulakh
(74) *Attorney, Agent, or Firm* — Elmore Patent Law Group, P.C.; Joseph C. Zucchero

(57) ABSTRACT

Provided herein are heterocyclic compounds of Formula (I), pharmaceutical compositions containing such a compound and their therapeutic uses, methods for their preparation, intermediate compounds, pharmaceutical compositions containing such a compound, and their therapeutic uses.

16 Claims, 2 Drawing Sheets

HETEROCYCLIC COMPOUNDS AND USES THEREOF

This application is a continuation of U.S. application Ser. No. 17/387,775, filed on Jul. 28, 2021, which is a continuation of U.S. patent application Ser. No. 17/121,484, filed on Dec. 14, 2020, which is a continuation of U.S. application Ser. No. 16/838,383, filed on Apr. 2, 2020, which is a continuation of U.S. application Ser. No. 16/441,610, filed Jun. 14, 2019, now U.S. Pat. No. 10,647,716, which is a continuation of U.S. application Ser. No. 15/977,772, filed May 11, 2018, now U.S. Pat. No. 10,370,374, which is a continuation of U.S. application Ser. No. 15/689,931, filed Aug. 29, 2017, now U.S. Pat. No. 9,975,894, which is a continuation of U.S. application Ser. No. 15/269,054, filed Sep. 19, 2016, now U.S. Pat. No. 9,771,363, which claims the benefit under 35 U.S.C. § 119(e) to U.S. Provisional Application Ser. No. 62/221,508 filed on Sep. 21, 2015, which are hereby incorporated by reference in their entirety.

BACKGROUND

The present disclosure relates to bromodomain proteins and compounds which modulate bromodomains, and uses therefor. Particular embodiments contemplate disease indications which are amenable to treatment by modulation of bromodomains by the compounds of the present disclosure.

SUMMARY

The present disclosure describes a select group of compounds that have demonstrated superior pharmacokinetics (PK) in comparison to compounds in earlier studies. More specifically, the compounds of Formula I and II disclosed herein are a selection invention of WO 2014/145051. The compounds of Formula I and II disclosed herein are novel compounds that are structurally unique from the specific compounds disclosed in WO 2014/145051 because the compounds in this disclosure have a di(pyridin-2-yl)methylene moiety that requires a $R^1$ substituent as defined in this disclosure. In contrast, the specific compounds disclosed in WO 2014/145051 that have a di(pyridin-2-yl)methylene moiety have a hydrogen at what would be the $R^1$ substituent as defined in this disclosure. As exemplified in this disclosure, the novel compounds described herein have demonstrated surprisingly much better PK properties compared to a structurally similar compound disclosed in WO 2014/145051, wherein the only structural difference is that the compound disclosed in WO 2014/145051 does not have the $R^1$ substituent as defined in this disclosure.

The present disclosure provides a compound of Formula (I):

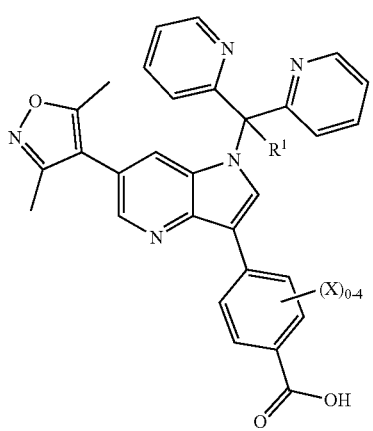

(I)

or a pharmaceutically acceptable salt, a solvate, a tautomer, an isomer, or a deuterated analog thereof, wherein:
$R^1$ is cyano, halo, or $(C_1-C_3)$alkyl optionally substituted with 1 to 3 substituents independently selected from the group consisting of halo, methyl, ethyl, methoxy and ethoxy; and
X, when present, is halo.

Another embodiment of this disclosure relates to a pharmaceutical composition comprising the compound of Formula (I) and a pharmaceutical acceptable excipient or carrier.

Another embodiment of this disclosure relates to a pharmaceutical composition comprising the compound of Formula (I) and a pharmaceutical acceptable excipient or carrier, and another therapeutic agent.

Another embodiment relates to a method for modulating bromodomain, said method comprising: administering to a subject a compound of Formula (I) or a pharmaceutical composition comprising the compound of Formula (I) and a pharmaceutical acceptable excipient or carrier.

Another embodiment relates to a method for treating a subject suffering or at risk of a disease or condition mediated by a bromodomain, said method comprising administering to the subject in need thereof an effective amount of a compound of Formula (I) or a pharmaceutical composition comprising the compound of Formula (I) and a pharmaceutical acceptable excipient or carrier.

DETAILED DESCRIPTION

I. Definitions

Figure 1:
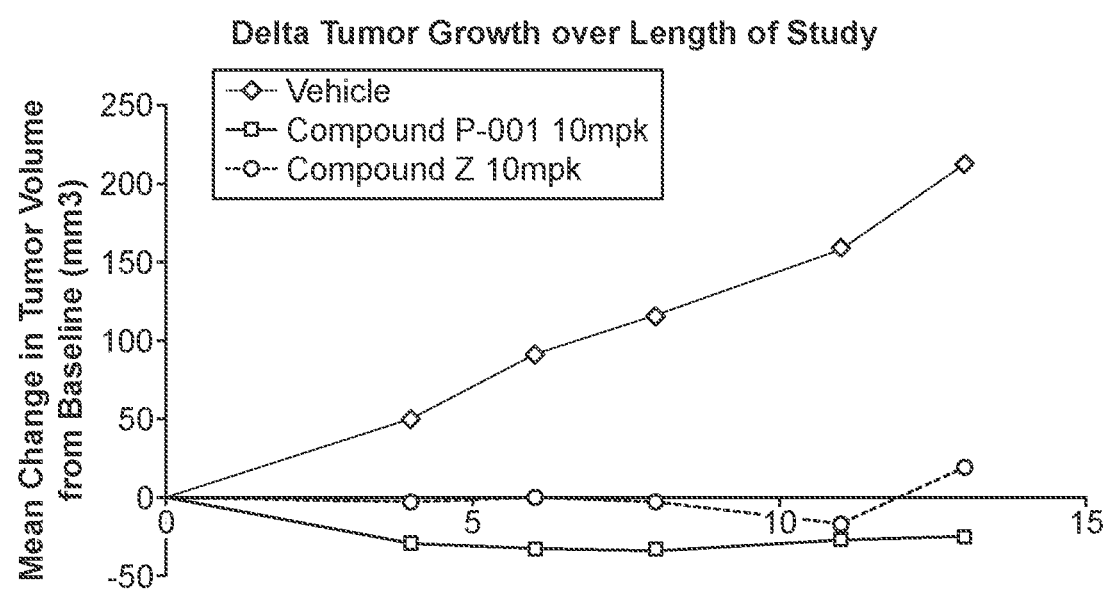
FIG. 1 depicts tumor volume over time measurements results as described in Example 5. The tumor volume over time measurements shown by the top line represents the vehicle. The tumor volume over time measurements shown by the bottom line represents Compound P-001 10 mg/kg. The tumor volume over time measurements shown by the middle line represents Compound Z 10 mg/kg.

As used herein, the following definitions apply unless clearly indicated otherwise:

It is noted here that as used in this specification and the appended claims, the singular forms "a," "an," and "the" include plural reference unless the context clearly dictates otherwise.

"Standard Error" as used herein is sample standard deviation divided by the square root of the sample size.

"Halogen" or "halo" means all halogens, that is, chloro (Cl), fluoro (F), bromo (Br), or iodo (I).

"Cyano" refers to the group —CN.

The term "alkyl," by itself or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5 or 6, carbon atoms. Further representative alkyl groups include straight and branched chain alkyl groups having 1, 2 or 3 carbon atoms.

"Optional" or "Optionally" as used throughout the specification means that the subsequently described event or circumstance may or may not occur, and that the description includes instances where the event or circumstance occurs and instances in which it does not. For example, the phrase "the aromatic group is optionally substituted with one or two alkyl substituents" means that the alkyl may but need not be present, and the description includes situations where the aromatic group is substituted with an alkyl group and situations where the aromatic group is not substituted with the alkyl group.

As used herein in connection with compounds of the present disclosure, the term "synthesizing" and like terms means chemical synthesis from one or more precursor materials.

"Protecting group" refers to a grouping of atoms that, when attached to a reactive group in a molecule, masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, Tetrahedron 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, $CH_2$=$CHCH_2$—, and the like, groups of the formula —C(O)R', wherein R' is, for example, methyl, phenyl, trifluoromethyl, and the like, groups of the formula —$SO_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

"Prodrug" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula (I) wherein a hydroxy, amino, carboxyl or sulfhydryl group in a compound of Formula (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula (I), and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

"Tautomer" means compounds produced by the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular formulae but differ in the nature or sequence of bonding of their atoms or in the arrangement of their atoms in space. Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007). Certain molecules claimed herein can exist in different enantiomeric and diastereomeric forms.

The compounds of the present disclosure may also contain unnatural proportions of atomic isotopes at one or more of the atoms that constitute such compounds. For example, the compounds may be radiolabelled with radioactive isotopes, such as for example tritium ($^3$H), iodine-125 ($^{125}$I), carbon-14 ($^{14}$C), carbon-11 ($^{11}$C) or fluorine-18 ($^{18}$F). All isotopic variations of the compounds of the present disclosure, whether radioactive or not, are intended to be encompassed within the scope of the present disclosure.

Certain molecules claimed in this patent can have one or more hydrogen atoms of the molecules replaced by one or more deuterium atoms including perdeuterated analogs, all such variants of these compounds are claimed. Further, it should be noted that the term "deuterated analog" refers to compounds where at least one hydrogen atom has been replaced by a deuterium atom. The term "deuterated" as used herein alone or as part of a group, means substituted deuterium atoms. When a particular position is designated as holding deuterium (stated as "D" or "deuterium"), it is understood that the abundance of deuterium at that position is substantially greater than the natural abundance of deuterium, which is 0.015% (i.e., at least 50.1% incorporation of deuterium).

The deuterated analog of the present disclosure may be a fully or partially deuterium substituted derivative. The deuterium substituted compound of the present disclosure can hold a fully or partially deuterium substituted alkyl, aryl or heteroaryl group. In one embodiment, the deuterium substituted compound of the present disclosure holds a fully or partially deuterium substituted alkyl group, e.g., —$CD_3$, $CD_2CD_3$, —$CD_2CD_2CD_3$ and the like. In another embodiment, the deuterium substituted compound of the present disclosure holds a fully or partially deuterium substituted aryl, such as phenyl, e.g., $C_6D_5$ or a fully or partially deuterium substituted heteroaryl, e.g., pyridyl-d3, and the like.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorous, fluorine, and chlorine, such as, but not limited to $^2H$ (deuterium, D) $^3H$ (tritium), $^{11}C$, $^{13}C$, $^{14}C$, $^{15}N$, $^{18}F$, $^{31}P$, $^{32}P$, $^{35}S$, $^{36}Cl$, an $^{125}I$. Unless otherwise stated, when a position is designated specifically as "H" or "hydrogen," the position is understood to have hydrogen at its natural abundance isotopic composition or its isotopes, such as deuterium (D) or tritium ($^3H$). Certain isotopically-labeled compounds of the present disclosure (e.g., those labeled with $^3H$ and $^{14}C$) are useful in compound and/or substrate tissue distribution assays. Tritiated (i.e., $^3H$) and carbon-14 (i.e., $^{14}C$) and fluorine-18 ($^{18}F$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those disclosed in the Schemes and in the Examples herein below, by substituting an isotopically labeled reagent for a non-isotopically labeled reagent.

Certain compounds of the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Such salts can be derived from pharmaceutically acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically acceptable organic bases include salts of primary, secondary, tertiary and quaternary amines, including substituted amines, cyclic amines, naturally-occurring amines and the like, such as arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, N,N'-dibenzylethylenediamine, chloroprocaine, choline, diethanolamine, meglumine (N-methyl-glucamine) and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically acceptable acids include acetic, trifluoroacetic, propionic, ascorbic, benzenesulfonic, benzoic, camphosulfonic, citric, ethanesulfonic, fumaric, glycolic, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, hydroiodic, carbonic, tartaric, p-toluenesulfonic, pyruvic, aspartic, benzoic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylaminosulfonic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

As used herein, the term "composition" refers to a formulation suitable for administration to an intended animal subject for therapeutic purposes that contains at least one pharmaceutically active compound and at least one pharmaceutically acceptable carrier or excipient.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

In the present context, the term "therapeutically effective" or "effective amount" indicates that a compound or amount of the compound when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

Bromodomains are a family of (~110 amino acid) structurally and evolutionary conserved protein interaction modules that specifically recognize acetylated lysines present in substrate proteins, notably histones. Bromodomains exist as components of large multidomain nuclear proteins that are associated with chromatin remodeling, cell signaling and transcriptional control. There are a total of 61 human bromodomains found within 46 human proteins. Examples of bromodomain-containing proteins with known functions include: (i) histone acetyltransferases (HATs), including CREBBP, GCN5, PCAF and TAFII250; (ii) methyltransferases such as ASH1L and MLL; (iii) components of chromatin-remodeling complexes such as Swi2/Snf2; and (iv) a number of transcriptional regulators (Florence et al. *Front. Biosci.* 2001, 6, D1008-1018).

As used herein, the terms "bromodomain mediated," "BET-mediated," "BRD2-mediated," "BRD3-mediated," "BRD4-mediated," and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role. Accordingly, another embodiment of the present disclosure relates to treating or lessening the severity of one or more diseases in which one or more of the bromodomain-containing proteins, such as BET proteins, such as BRD2, BRD3, BRD4, and/or BRDT, or a mutant thereof, are known to play a role. For example, a disease or condition in which the biological function of bromodomain affects the development and/or course of the disease or condition, and/or in which modulation of bromodomain alters the development, course, and/or symptoms. Bromodomain mediated disease or condition includes a disease or condition for which bromodomain inhibition provides a therapeutic benefit, e.g. wherein treatment with bromodomain inhibitors, including compounds described herein, provides a therapeutic benefit to the subject suffering from or at risk of the disease or condition. The term "inhibiting bromodomain" or "bromodomain inhibitor" means a compound which inhibits the binding of a bromodomain with its cognate acetylated proteins, for example, the bromodomain inhibitor is a compound which inhibits the binding of a bromodomain to acetylated lysine residues.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an protein such as a bromodomain. Generally a ligand or modulator will be a small molecule, where "small molecule refers to a compound with a molecular weight of 1500 Daltons or less, or preferably 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($K_D$) of 1 mM or less, 1 µM or less, 100 nM or less, 10 nM or less, or 1 nM or less.

As used herein, the term "modulating" or "modulate" refers to an effect of altering a biological activity, especially a biological activity associated with a particular biomolecule such as a bromodomain protein. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "prevent," "preventing," "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or reacquiring a disorder or condition or one or more of its attendant symptoms.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

In addition, abbreviations as used herein have respective meanings as follows:

| | |
|---|---|
| °C. | Degree Celsius |
| % F | Bioavailability (%) |
| AUC | Area under the curve |
| BOC | tert-Butoxy carbonyl |
| BSA | Bovine serum albumin |
| CL | Apparent total body clearance of the drug from plasma |
| $C_{max}$ | Maximum plasma concentration |
| DMAP | 4-dimethylaminopyridine |
| DMSO | Dimethylsulfoxide |
| DTT | Dithiothreitol |
| EtOAc | Ethyl acetate |
| $Et_2O$ | Diethyl ether |
| FBS | Fetal bovine serum |
| g | Gram |
| HEPES | 4-(2-hydroxyethyl)-1-piperazineethanesulfonic acid |
| HPLC | High performance liquid chromatography |
| hr(s) | Hour(s) |
| Kg or Kg | Kilogram |
| L | Liter |
| LC-MS | Liquid chromatography-mass spectrometry |
| LC/MS/MS | Liquid chromatography-tandem mass spectrometry |
| M | Molar |
| MeOH | Methanol |
| MS (ESI) | Mass spectrometry electrospray ionization |
| mg | Milligram |
| min | Minutes |
| mE or ml | Milliliter |
| mm | Millimeter |
| mM | Millimolar |
| mmol | Millimole |
| mol | Mole |
| MTD | Maximum tolerated dose |
| N | Normal |
| nm | nanometers |
| nM | Nanomolar |
| PD | pharmacodynamics |
| po | By mouth |
| QD | Once daily |
| $T_{1/2}$ | Half-life |
| $T_{max}$ | Peak time |
| THF | Tetrahydrofuran |
| $V_{ss}$ | Apparent volume of distribution at steady state |
| µg | Microgram |
| µL | Microliter |
| µM | Micromolar |

II. General

The present disclosure concerns compounds of Formula (I), (II), and all sub-generic formulae, compounds as recited in the claims, and compounds described herein that are modulators of bromodomains and the use of such compounds in the treatment of diseases or conditions. Also disclosed herein are compounds useful for the synthesis of compounds of Formula (I) and (II).

III. Compounds

In some embodiments, the present disclosure provides compounds of Formula (I) and all sub-generic formulae and compounds disclosed herein, or a pharmaceutically acceptable salt, hydrate, solvate, tautomer or isomer thereof.

In one embodiment, the present disclosure provides a compound of Formula (I):

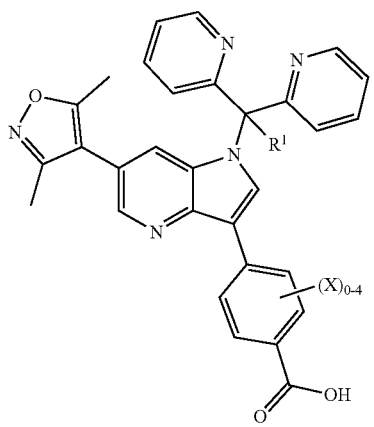

(I)

or a pharmaceutically acceptable salt, a solvate, a tautomer, an isomer, or a deuterated analog thereof, wherein:

$R^1$ is cyano, halo, or $(C_1-C_3)$alkyl optionally substituted with 1 to 3 substituents independently selected from the group consisting of halo, methyl, ethyl, methoxy and ethoxy; and X, when present, is halo.

In another embodiment of Formula (I), $R^1$ is $(C_1-C_2)$alkyl, cyano or fluoro.

In another embodiment of Formula (I), $R^1$ is methyl, cyano or fluoro.

In another embodiment of Formula (I), $R^1$ is $(C_1-C_2)$alkyl. In another embodiment of Formula (I), $R^1$ is methyl. In another embodiment of Formula (I), $R^1$ is cyano. In another embodiment of Formula (I), $R^1$ is halo. In another embodiment of Formula (I), $R^1$ is fluoro.

In another embodiment of Formula (I), $R^1$ is $(C_1-C_2)$alkyl optionally substituted with 1 to 3 substituents independently selected from the group consisting of halo, methyl, ethyl, methoxy and ethoxy. In another embodiment of Formula (I), $R^1$ is methyl optionally substituted with 1 to 3 substituents independently selected from the group consisting of halo, methyl, ethyl, methoxy and ethoxy.

In another embodiment of Formula (I), X is absent. In another embodiment of Formula (I), X is halo. In another embodiment of Formula (I), X is fluoro. In another embodiment of Formula (I), X is chloro.

In another embodiment of Formula (I), $R^1$ is $(C_1-C_3)$alkyl, and X is absent. In another embodiment of Formula (I), $R^1$ is $(C_1-C_3)$alkyl, and X is halo. In another embodiment of Formula (I), $R^1$ is $(C_1-C_3)$alkyl and X is fluoro. In another embodiment of Formula (I), $R^1$ is $(C_1-C_3)$alkyl and X is chloro. In another embodiment of Formula (I), $R^1$ is $(C_1-C_2)$alkyl and X is absent. In another embodiment of Formula (I), $R^1$ is $(C_1-C_2)$alkyl and X is halo. In another embodiment of Formula (I), $R^1$ is $(C_1-C_2)$alkyl and X is fluoro. In another embodiment of Formula (I), $R^1$ is $(C_1-C_2)$alkyl and X is chloro.

In another embodiment of Formula (I), $R^1$ is $(C_1-C_3)$alkyl optionally substituted with 1 to 3 substituents independently selected from the group consisting of halo, methyl, ethyl, methoxy and ethoxy, and X is absent. In another embodiment of Formula (I), $R^1$ is $(C_1-C_3)$alkyl optionally substituted with 1 to 3 substituents independently selected from the group consisting of halo, methyl, ethyl, methoxy and ethoxy, and X is halo. In another embodiment of Formula (I), $R^1$ is $(C_1-C_3)$alkyl optionally substituted with 1 to 3 substituents independently selected from the group consisting of halo, methyl, ethyl, methoxy and ethoxy, and X is fluoro. In another embodiment of Formula (I), $R^1$ is $(C_1-C_3)$alkyl and X is chloro.

In another embodiment of Formula (I), $R^1$ is $(C_1-C_2)$alkyl optionally substituted with 1 to 3 substituents independently selected from the group consisting of halo, methyl, ethyl, methoxy and ethoxy, and X is absent.

In another embodiment of Formula (I), $R^1$ is $(C_1-C_2)$alkyl optionally substituted with 1 to 3 substituents independently selected from the group consisting of halo, methyl, ethyl, methoxy and ethoxy, and X is halo. In another embodiment of Formula (I), $R^1$ is $(C_1-C_2)$alkyl optionally substituted with 1 to 3 substituents independently selected from the group consisting of halo, methyl, ethyl, methoxy and ethoxy, and X is fluoro. In another embodiment of Formula (I), $R^1$ is $(C_1-C_2)$alkyl optionally substituted with 1 to 3 substituents independently selected from the group consisting of halo, methyl, ethyl, methoxy and ethoxy, and X is chloro.

In another embodiment of Formula (I), $R^1$ is methyl and X is absent. In another embodiment of Formula (I), $R^1$ is methyl and X is halo. In another embodiment of Formula (I), $R^1$ is methyl and X is fluoro. In another embodiment of Formula (I), $R^1$ is methyl and X is chloro.

In another embodiment of Formula (I), $R^1$ is methyl optionally substituted with 1 to 3 substituents independently selected from the group consisting of halo, methyl, ethyl, methoxy and ethoxy, and X is absent. In another embodiment of Formula (I), $R^1$ is methyl optionally substituted with 1 to 3 substituents independently selected from the group consisting of halo, methyl, ethyl, methoxy and ethoxy, and X is halo. In another embodiment of Formula (I), $R^1$ is methyl optionally substituted with 1 to 3 substituents independently selected from the group consisting of halo, methyl, ethyl, methoxy and ethoxy, and X is fluoro. In another embodiment of Formula (I), $R^1$ is methyl optionally substituted with 1 to 3 substituents independently selected from the group consisting of halo, methyl, ethyl, methoxy and ethoxy, and X is chloro.

Another embodiment of Formula (I) is the compound of Formula (II):

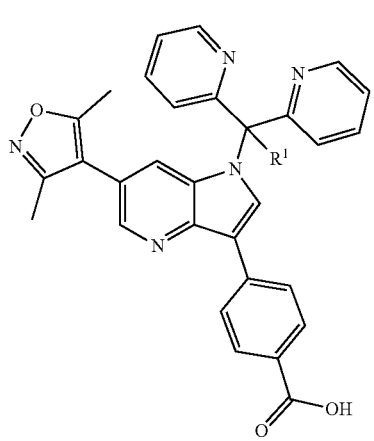

(II)

or a pharmaceutically acceptable salt, a solvate, a tautomer, an isomer, or a deuterated analog thereof, wherein:

$R^1$ is cyano, halo, or $(C_1-C_3)$alkyl optionally substituted with 1 to 3 substituents independently selected from the group consisting of halo, methyl, ethyl, methoxy and ethoxy.

In another embodiment of Formula (II), $R^1$ is ($C_1$-$C_2$) alkyl, cyano or fluoro.

In another embodiment of Formula (II), $R^1$ is methyl, cyano or fluoro.

In another embodiment of Formula (II), $R^1$ is cyano, halo, or ($C_1$-$C_2$) optionally substituted with one or more halo. In another embodiment of Formula (II), $R^1$ is cyano, halo, or methyl optionally substituted with one or more halo. In another embodiment of Formula (II), $R^1$ is methyl. In another embodiment of Formula (II), $R^1$ is methyl optionally substituted with 1-3 halo. In another embodiment of Formula (II), $R^1$ is methyl optionally substituted with 1-3 chloro. In another embodiment of Formula (II), $R^1$ is methyl optionally substituted with 1-3 fluoro. In another embodiment of Formula (II), $R^1$ is cyano. Another embodiment of Formula (II), $R^1$ is fluoro.

In another embodiment of Formula (II), $R^1$ is cyano, halo, or ($C_1$-$C_2$) optionally substituted with 1 to 3 substituents independently selected from the group consisting of halo, methyl, ethyl, methoxy and ethoxy. In another embodiment of Formula (II), $R^1$ is methyl optionally substituted with 1 to 3 substituents independently selected from the group consisting of halo, methyl, ethyl, methoxy and ethoxy.

Another embodiment of the compound of Formula I or II is a compound of Table I or a pharmaceutically acceptable salt, a solvate, a tautomer, an isomer, or a deuterated analog of any of the compounds in Table I:

TABLE I

| Number | Structure | Name | $[M + H^+]^+$ |
|---|---|---|---|
| P-001 | 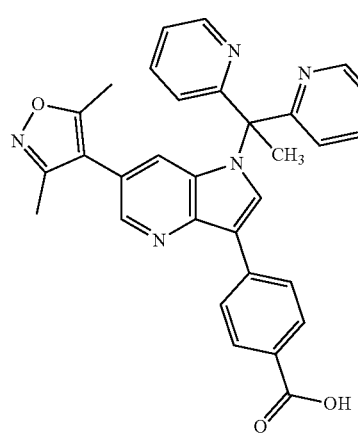 | 4-(1-(1,1-di(pyridin-2-yl)ethyl)-6-(3,5-dimethylisoxazol-4-yl)-1H-pyrrolo[3,2-b]pyridin-3-yl)benzoic acid | 515.56 |
| P-004 | 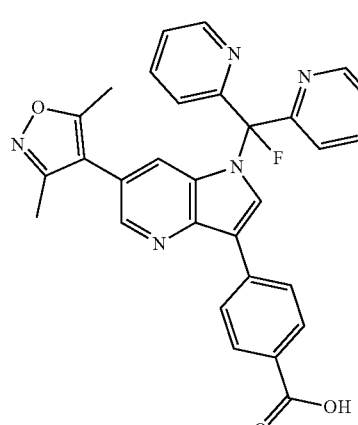 | 4-(6-(3,5-dimethylisoxazol-4-yl)-1-(fluorodi(pyridin-2-yl)methyl)-1H-pyrrolo[3,2-b]pyridin-3-yl)benzoic acid | 519.52 |

TABLE I-continued

| Number | Structure | Name | [M + H⁺]⁺ |
|---|---|---|---|
| P-006 | 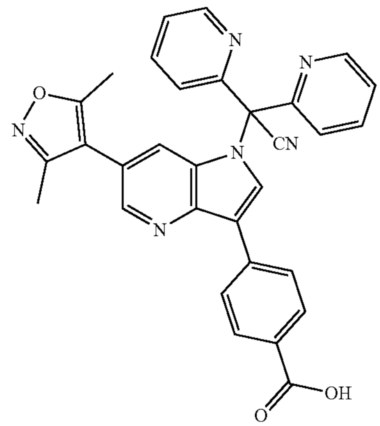 [SMILES: Cc1noc(C)c1-c1cnc2c(-c3ccc(C(=O)O)cc3)cn(C(C#N)(c3ccccn3)c3ccccn3)c2c1] | 4-(1-(cyanodi(pyridin-2-yl)methyl)-6-(3,5-dimethylisoxazol-4-yl)-1H-pyrrolo[3,2-b]pyridin-3-yl)benzoic acid | 526.54 |

Another embodiment of this disclosure relates to a compounds that are intermediate compounds useful for the synthesis of the compound of Formula (I), Formula (II), or of the compounds listed in Table I, wherein the intermediate compound is one of the following Formula:

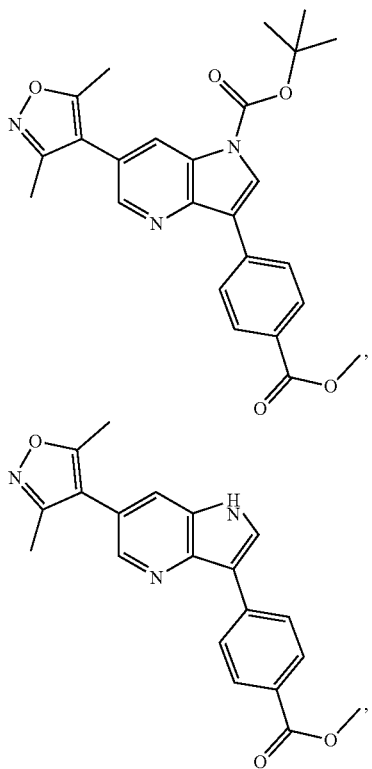

or a pharmaceutically acceptable salt, a solvate, a tautomer, an isomer, or a deuterated analog thereof.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, Advanced Organic Chemistry; Reactions, Mechanisms and Structure, New York, McGraw Hill. Thus, the techniques useful to synthesize a potential modulator of bromodomain function are readily available to those skilled in the art of organic chemical synthesis.

Alternative Compound Forms or Derivatives

Compounds contemplated herein are described with reference to both generic formulae and specific compounds. In addition, compounds disclosed herein may exist in a number of different forms or derivatives, all within the scope of the present disclosure. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the present disclosure also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 1-position of the 1H-pyrrolo[2,3-b]pyridine ring, or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, CA, 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application. Ser. No. 10/656, 838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86 (7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present disclosure. Unless specified to the contrary, all such stereoisomeric forms are included within the formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein and recited in any of the claims can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the present disclosure may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfate, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see Remington's Pharmaceutical Sciences, 19$^{th}$ ed., Mack Publishing Co., Easton, PA, Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the present disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the present disclosure with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

IV. Formulations and Administration

In another aspect, the present disclosure provides pharmaceutical compositions comprising/including a pharmaceutically acceptable carrier, excipient and/or diluent and a compound of the present disclosure described herein or a pharmaceutically acceptable salt or solvate thereof. In an exemplary embodiment, the present disclosure provides a pharmaceutical formulation comprising/including a compound as described herein. In some embodiments, the present disclosure provides pharmaceutical composition comprising/including a compound of Formulae (I) or (II); or a pharmaceutically acceptable salt, a solvate, a tautomer, an isomer, or a deuterated analog of Formulae (I) or (II); or any of the compounds in Table I, and a pharmaceutically acceptable carrier, excipient and/or diluents.

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, $21^{st}$ edition, Lippincott, Williams and Wilkins, Philadelphia, PA, 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 400-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the present disclosure (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

In some embodiments, oral administration may be used. Pharmaceutical preparations for oral use can be formulated into conventional oral dosage forms such as discreet units capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone); oily excipients, including vegetable and animal oils, such as sunflower oil, olive oil, or cod-liver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations, such as unit dosages. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures. Oral fluids such as solutions, syrups and elixirs can be prepared in dosage unit form so that a given quantity contains a predetermined amount of the compound.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than Cu). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the present disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present disclosure provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components. The compounds as disclosed herein may be used in adjuvant or neoadjuvant therapy in combination with other therapy or therapeutic agents as described herein.

V. Disease Indications and Modulations of Bromodomains

Exemplary Diseases Associated with Bromodomains

Members of the BET (Bromodomain and Extra Terminal) family of bromodomain proteins (BRD2, BRD3, BRD4 and BRDT) have been associated with a variety of disorders including neurological diseases, autoimmune and inflammatory diseases, metabolic diseases (Muller et al. *Expert Rev. Mol. Med.* 2011, Sep. 13; 13:e29; Prinjha et al. *Trends Pharmacol. Sci.* 2012, 33, 146-153; Belkina et al. *J. Immunol.* 2013, 190, 3670-3678; and Belkina et al. *Nature Rev. Cancer* 2012, 12, 465-477) and cancers (Alsarraj et al. *International Journal of Breast Cancer* 2012, 1-7; Barbieri et al. *Briefings in Functional Genomics* 2013, 1-12; Blobel et al. *Cancer Cell* 2011, 20, 287-288; Dang *Cell* 2012, 149, 22-35). In addition, some viruses make use of these proteins to tether their genomes to the host cells chromatin, as part of the process of viral replication (You et al *Cell,* 2004 117, 349-60).

The compounds of Formulae (I) or (II), or any of the compounds as described herein, are useful for treating disorders related to one or more proteins involved in epigenetic regulation, such as proteins containing acetyl-lysine recognition motifs, i.e., bromodomains (e.g., BET proteins, such as BRD2, BRD3, BRD4, and/or BRDT), and e.g., diseases related to abnormal expression of bromodomains, including cell proliferative disorders, cancers, chronic autoimmune, inflammatory conditions, among others.

The presence of bromodomains has been associated with a number of different types of cancers, and other diseases and conditions, as described below. Bromodomain inhibitors such as compounds of Formulae (I) or (II); or a pharmaceutically acceptable salt, a solvate, a tautomer, an isomer, or a deuterated analog of Formulae (I) or (II); all embodiments of Formulae I or II described herein; or any of the compounds as described in Table I, are useful in the treatment of systemic or tissue inflammation, inflammatory responses to infection or hypoxia, cellular activation and proliferation, lipid metabolism, fibrosis and in the prevention and treatment of viral infections.

Bromodomain inhibitors such as compounds of Formulae (I) or (II); or a pharmaceutically acceptable salt, a solvate, a tautomer, an isomer, or a deuterated analog of Formulae (I) or (II); all embodiments of Formulae I or II described herein; or any of the compounds as described in Table I, are useful in the prevention and treatment of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors such as compounds of Formulae (I) or (II); or a pharmaceutically acceptable salt, a solvate, a tautomer, an isomer, or a deuterated analog of Formulae (I) or (II); all embodiments of Formulae I or II described herein; or any of the compounds as described in Table I, are useful in the prevention and treatment of acute inflammatory conditions, including, but not limiting to, such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

Bromodomain inhibitors such as compounds of Formulae (I) or (II); or a pharmaceutically acceptable salt, a solvate, a tautomer, an isomer, or a deuterated analog of Formulae (I) or (II); all embodiments of Formulae I or II described herein; or any of the compounds as described in Table I, are useful in the prevention and treatment of autoimmune and inflammatory diseases or conditions which involve inflammatory responses to infections with bacteria, viruses, such as herpes virus, human papilloma virus, adenovirus and poxvirus and other DNA viruses; fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors such as compounds of Formulae (I) or (II); or a pharmaceutically acceptable salt, a solvate, a tautomer, an isomer, or a deuterated analog of Formulae (I) or (II); all embodiments of Formulae I or II described herein;

or any of the compounds as described in Table I, are useful in the prevention and treatment of diseases or conditions associated with ischemia-reperfusion injury, including, but not limiting to, myocardial infarction, cerebro-vascular ischemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors such as compounds of Formulae (I) or (II); or a pharmaceutically acceptable salt, a solvate, a tautomer, an isomer, or a deuterated analog of Formulae (I) or (II); all embodiments of Formulae I or II described herein; or any of the compounds as described in Table I, are useful in the prevention and treatment of hypercholesterolemia, atherosclerosis and Alzheimer's disease.

Bromodomain inhibitors such as compounds of Formulae (I) or (II); or a pharmaceutically acceptable salt, a solvate, a tautomer, an isomer, or a deuterated analog of Formulae (I) or (II); all embodiments of Formulae I or II described herein; or any of the compounds as described in Table I, are useful in the prevention and treatment of cancers including, but not limiting to, hematological, epithelial including lung, breast and colon carcinomas, midline carcinomas, mesenchymal, hepatic, renal, neurological tumors, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

Bromodomain Activity Assays

A number of different assays for bromodomain activity can be utilized for assaying for active modulators and/or determining specificity of a modulator for a particular bromodomain or group. In addition to the assay mentioned in the Examples below, one of ordinary skill in the art will know of other assays that can be utilized and can modify an assay for a particular application.

In certain embodiments, compounds of Formulae (I) or (II), or a compounds set forth in Table I. have an $IC_{50}$ of less than less than 100 nM, less than 50 nM, less than 20 nM, less than 10 nM, less than 5 nM, or less than 1 nM as determined in a generally accepted bromodomain activity assay or a bromodomain activity assay as described herein. In some embodiments, the assay for measuring bromodomain activity includes an assay (e.g., biochemical or cell-bases assays) such as described in Example 6 or an assay known in the art.

Modulation of Bromodomain

In another aspect, the present disclosure provides a method for modulating or inhibiting a bromodomain protein. The method includes administering to a subject an effective amount of a compound of a compounds of Formulae (I) or (II); or a pharmaceutically acceptable salt, a solvate, a tautomer, an isomer, or a deuterated analog of Formulae (I) or (II); or any of the compounds as described in Table I; or a composition comprising a compound of any of the formulae as described herein, thereby, modulating or inhibiting the bromodomain. In some embodiments, the method includes contacting a cell in vivo or in vitro with a compound of Formulae (I) or (II); or a pharmaceutically acceptable salt, a solvate, a tautomer, an isomer, or a deuterated analog of Formulae (I) or (II); all embodiments of Formulae I or II described herein; or any of the compounds as described in Table I, or a composition comprising a compound of any of the formulae as described herein.

VI. Methods for Treating Conditions Mediated by Bromodomain

In another aspect, the present disclosure provides a method for treating a subject suffering from or at risk of a bromodomain mediated diseases or conditions, wherein inhibition of bromodomain plays a role or provides a benefit. The method includes administering to the subject an effective amount of a compound of Formulae (I) or (II); or a pharmaceutically acceptable salt, a solvate, a tautomer, an isomer, or a deuterated analog of Formulae (I) or (II); or any of the compounds as described in Table I, or a composition comprising a compound of any of the formulas as described herein. In certain embodiments, the method involves administering to the subject an effective amount of any one or more compound(s) as described herein in combination with one or more other therapies or therapeutic agents for the disease or condition. In some embodiments, the method involves administering to the subject an effective amount of any one or more compound(s) as described herein in combination with one or more other therapeutic agents for the disease or condition.

In some embodiments, the present disclosure provides a method of suppressing undesired proliferation of tumor cells mediated by bromodomain. The method includes contacting tumor cells with an effective amount of a compound of a compound of any of Formulae (I) or (II), or any of the compounds set forth in Table I, or a pharmaceutically acceptable salt, hydrate, solvate, tautomer or isomer thereof, or a composition comprising a compound as described herein. In some instances, the tumor cells are mediated by BET protein, BRD4 protein or a mutant thereof.

In certain embodiments, the present disclosure provides a method of treating a patient, where inhibition of bromodomain (e.g., BET protein or BRD4 protein) provides a benefit. The method includes administering to the patient in need thereof an effective amount of a compound of any of Formulae (I) or (II), or any of the compounds set forth in Table I, or a pharmaceutically acceptable salt, hydrate, solvate, tautomer or isomer thereof, or a composition comprising a compound as described herein.

In some embodiments, the present disclosure provides methods for treating a subject suffering or at risk of a disease or condition mediated by a bromodomain, said method comprising administering to the subject in need thereof an effective amount of a compound of Formulae (I) or (II); or a pharmaceutically acceptable salt, a solvate, a tautomer, an isomer, or a deuterated analog of Formulae (I) or (II);or any of the compounds in Table I, or any of the pharmaceutical compositions thereof described herein, and the disease or condition is a cancer, an autoimmune condition, an inflammatory condition or a combination thereof.

In some embodiments, the diseases or conditions treatable with the compounds of the present disclosure include, but are not limited to, a cancer, e.g., hematological, epithelial including lung, breast and colon carcinomas, midline carcinomas, mesenchymal, hepatic, renal, neurological tumors, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In certain embodiments, the cancer treatable with the compounds of the present disclosure is selected from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor. In other embodiments, the cancers or tumors treatable with the compounds of the present disclosure include benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome. In another embodiment, the diseases or conditions treatable with the compounds of the present disclosure include non-small cell lung cancer, small cell lung cancer, ovarian cancer, melanoma, midline carcinomas, breast cancer, lymphomas, neuroblastoma, or castration resistant prostate cancer, myelofibrosis, myelodysplastic syndromes, or acute myeloid leukemia. In another embodiment, the diseases or conditions treatable with the compounds of the present disclosure include non-small cell lung cancer, small cell lung cancer, ovarian cancer, melanoma, neuroblastoma, and castration resistant prostate cancer.

In another embodiment of this disclosure, the disease or condition that can be treated by the compounds of the present disclosure is a lysosomal storage disorder. Non-limiting examples of lysosomal storage disorders include mucolipodosis, alpha-mannosidosis; aspartylglucosaminuria; Batten disease; beta-mannosidosis; cystinosis; Danon disease; Fabry disease; Farber disease; fucosidosis; galactosialidosis; Gaucher disease; gangliosidosis (e.g., GM1 gangliosidosis and GM2-gangliosidosis AB variant); Krabbe disease; metachromatic leukodystrophy; mucopolysaccharidoses disorders (e.g., MPS 1—Hurler syndrome, MPS II—Hunter syndrome, MPS III—Sanfilippo (A,B,C,D), MPS IVA—Morquio, MPS IX—hyaluronidase, deficiency, MPS VI—Maroteaux-Lamy, or MPS VII—Sly syndrome); mucolipidosis type I (Sialidosis); Mucolipidosis type II (I-Cell disease); Mucolipidosis type III (Pseudo-Hurler polydystrophy); Mucolipidosis type IV; multiple sulfatase deficiency; Niemann—Pick types A, B, C; Pompe disease (glycogen storage disease); pycnodysostosis; Sandhoff disease; Schindler disease; Salla disease/sialic acid storage disease; Tay—Sachs; and Wolman disease.

In some embodiments, the present disclosure provides methods for treating an autoimmune and inflammatory disease or condition in a subject by administration of an effective amount of a compound of Formulae (I) or (II); or a pharmaceutically acceptable salt, a solvate, a tautomer, an isomer, or a deuterated analog of Formulae (I) or (II);or any of the compounds in Table I, or any of the pharmaceutical compositions thereof described herein. The diseases or conditions treatable with the compounds of the present disclosure include, but are not limited to, inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease. In certain embodiments, the diseases and conditions treatable with the compounds of the present disclosure include systemic or tissue inflammation, inflammatory responses to infection or hypoxia, cellular activation and proliferation, lipid metabolism, fibrosis and viral infections.

In some embodiments, the present disclosure provides methods for treating a subject suffering or at risk of chronic autoimmune and inflammatory conditions by administering to the subject in need thereof an effective amount of a compound of Formulae (I) or (II); or a pharmaceutically acceptable salt, a solvate, a tautomer, an isomer, or a deuterated analog of Formulae (I) or (II); or any of the compounds in Table I, or any of the pharmaceutical compositions thereof described herein. The chronic autoimmune and inflammatory conditions treatable with the compounds of the present disclosure include, but are not limited to, rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs. In one embodiment, the disease or condition is sepsis, burns, pancreatitis, major trauma, hemorrhage or ischemia. In another embodiment, the disease or condition treatable with the compounds of the present disclosure includes sepsis, sepsis syndrome, septic shock or endotoxaemia. In another embodiment, the disease or condition treatable with the compounds of the present disclosure includes acute or chronic pancreatitis. In another embodiment, the disease or condition treatable with the compounds of the present disclosure includes burns.

In some embodiments, the present disclosure provides methods for treating a subject suffering or at risk of acute inflammatory conditions by administering to the subject in need thereof an effective amount of a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein. The acute inflammatory conditions, include, but are not limited to, acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

In some embodiments, the present disclosure provides methods for treating a subject suffering or at risk of autoimmune and inflammatory diseases or conditions by administering to the subject in need thereof an effective amount of a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein. The autoimmune and inflammatory diseases or conditions treatable with the compounds of the present disclosure which involve inflammatory responses to infections with bacteria, viruses, such as herpes virus, human papilloma virus, adenovirus and poxvirus and other DNA viruses; fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

In some embodiments, the present disclosure provides methods for treating a subject suffering or at risk of ischemia-reperfusion injury by administering to the subject in need thereof an effective amount of a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein. The ischemia-reperfusion injury, includes, but is not limited to, myocardial infarction, cerebro-vascular ischemia (stroke), acute coronary syndromes, renal reperfusion injury, organ transplantation, coronary artery bypass grafting, cardio-pulmonary bypass procedures, pulmonary, renal, hepatic, gastro-intestinal and peripheral limb embolism.

In some embodiments, the present disclosure provides methods for treating a subject suffering or at risk of hypercholesterolemia, atherosclerosis or Alzheimer's disease by administering to the subject in need thereof an effective amount of a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein.

In some embodiments, the present disclosure provides methods for treating any bromodomain mediated disease or condition, including any bromodomain mutant mediated disease or condition in an animal subject in need thereof, wherein the method involves administering to the subject an effective amount of any one or more compound(s) as described herein or any pharmaceutical compositions thereof described herein. In certain embodiments, the method involves administering to the subject an effective amount of any one or more compound(s) as described herein or any pharmaceutical compositions thereof described herein in combination with one or more other therapies or therapeutic agents for the disease or condition.

In some embodiments, a compound of Formulae (I) or (II); or a pharmaceutically acceptable salt, a solvate, a tautomer, an isomer, or a deuterated analog of Formulae (I) or (II); or any of the compounds in Table I, is a bromodomain inhibitor and has an $IC_{50}$ of less than 500 nM, less than 100 nM, less than 50 nM, less than 20 nM, less than 10 nM, less than 5 nM, or less than 1 nM as determined in a generally accepted bromodomain activity assay. In some embodiments, a compound as described herein will have an $IC_{50}$ of less than 500 nM, less than 100 nM, less than 50 nM, less than 20 nM, less than 10 nM, less than 5 nM, or less than 1 nM with respect to bromodomain, e.g., BET protein, BRD2, BRD3 or BRD4 protein. In some embodiments, a compound as described herein will selectively inhibit one or more bromodomain relative to one or more other proteins.

In some embodiments, the present disclosure provides a method for inhibiting a bromodomain or mutant bromodomain. The method includes contacting a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein, with a cell or a bromodomain protein in vitro or in vivo.

In certain embodiments, the present disclosure provides use of a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein in the manufacture of a medicament for the treatment of a disease or condition as described herein. In other embodiments, the present disclosure provides a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein for use in treating a disease or condition as described herein.

Combination Therapy

Bromodomain modulators may be usefully combined with another pharmacologically active compound, or with two or more other pharmacologically active compounds, particularly in the treatment of cancer and other diseases and indications described herein. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the present disclosure provides methods for treating a bromodomain or mutant bromodomain mediated disease or condition in an animal subject in need thereof, wherein the method involves administering to the subject an effective amount of any one or more compound(s) as described herein, or one or more compounds of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein, in combination with one or more other therapeutic agent as described herein. In certain embodiments, the present disclosure provides methods for treating bromodomain or mutant bromodomain mediated disease or condition in an animal subject in need thereof, wherein the method involves administering to the subject an effective amount of any one or more compound(s) of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein, in combination with one or more other therapies for the disease or condition.

In some embodiments, the present disclosure provides a composition, e.g., a pharmaceutical composition comprising a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein, and one or more other therapeutic agents. In some embodiments, the one or more other therapeutic agents are selected from an alkylating agent, including, but not limiting to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafururacil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limiting to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limiting to, demecolcine, homoharringtonine, vinblastine, vincristine, vindesine, vinflunine, and vinorelbine; an antiangiogenic agent, including, but not limiting to, AE-941 (GW786034, Neovastat), ABT-510, 2-methoxyestradiol, lenalidomide, and thalidomide; a topoisomerase inhibitor, including, but not limiting to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, LGX818, BGB-283, pexidartinib (PLX3397) and vatalanib; a targeted signal transduction inhibitor including, but not limiting to bortezomib, geldanamycin, and rapamycin; a biological response modifier, including, but not limiting to, imiquimod, interferon-α, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus), PI3K inhibitors (e.g. BEZ235, GDC-0941, XL147, XL765, •BMK120), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane). In one embodiment, the method of treating a cancer involves administering to the subject an effective amount of a composition including any one or more compound(s) of Formulae (I) or (II); or a pharmaceutically acceptable salt, a solvate, a tautomer, an isomer, or a deuterated analog of Formulae (I) or (II); or any of the compounds in Table I, in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In another embodiment, the chemotherapeutic agent is a Mek inhibitor. Exemplary Mek inhibitors include, but are not limited to, AS703026, AZD6244 (Selumetinib), AZD8330, BIX 02188, CI-1040 (PD184352), GSK1120212 (JTP-74057), PD0325901, PD318088, PD98059, RDEA119 (BAY 869766), TAK-733 and U0126-EtOH. In another embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate(BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib (TAK 165), Neratinib (HKI-272), NVP-BHG712, OSI-420 (Desmethyl Erlotinib,CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, quizartinib, Cabozantinib, XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin). In another embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441, Tarceva (Erlotinib, OSI-774), CUDC-101 and WZ4002. In another embodiment, the therapeutic agent for combination is a c-Fms and/or c-Kit inhibitor as described in US Patent Application Publication Nos. 2009/0076046 and 2011/0112127, which are incorporated herein by reference in their entirety and for all purposes. In one embodiment, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In some embodiments, a bromodomain modulator, particularly a compound of any of Formulae (I) or (II); or a pharmaceutically acceptable salt, a solvate, a tautomer, an isomer, or a deuterated analog of Formulae (I) or (II); or any of the compounds in Table I, may be administered simultaneously, sequentially or separately in combination with one or more agents as described above.

In some embodiments, the present disclosure provides a composition, e.g., a pharmaceutical composition comprising a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein, and one or more other therapeutic agents. In some embodiments, the one or more other therapeutic agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafururacil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limiting to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limiting to, demecolcine, homoharringtonine, vinblastine, vincristine, vindesine, vinflunine, and vinorelbine; an antiangiogenic agent, including, but not limiting to, AE-941 (GW786034, Neovastat), ABT-510, 2-methoxyestradiol, lenalidomide, and thalidomide; a topoisomerase inhibitor, including, but not limiting to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, paradox breakers (such as PLX8394 or PLX7904), LGX818, BGB-283, pexidartinib (PLX3397) and vatalanib; a targeted signal transduction inhibitor including, but not limiting to bortezomib, geldanamycin, and rapamycin; a biological response modifier, including, but not limiting to, imiquimod, interferon-α, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus, INK28, AZD8055, PI3K inhibitors (e.g. BEZ235, GDC-0941, XL147, XL765, BMK120), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane). In one embodiment, the method of treating a cancer involves administering to the subject an effective amount of a composition including any one or more compound(s) of Formulae (I) or (II); or a pharmaceutically acceptable salt, a solvate, a tautomer, an isomer, or a deuterated analog of Formulae (I) or (II); or any of the compounds in Table I, in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In another embodiment, the chemotherapeutic agent is a Mek inhibitor. Exemplary Mek inhibitors include, but are not limited to, AS703026, AZD6244 (Selumetinib), AZD8330, BIX 02188, CI-1040 (PD184352), GSK1120212 (also known as trametinib or JTP-74057), cobimetinib, PD0325901, PD318088, PD98059, RDEA119(BAY 869766), TAK-733 and U0126-EtOH. In another embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate (BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib(TAK 165), Neratinib (HKI-272), NVP-BHG712, OSI-420 (Desmethyl Erlotinib,CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, quizartinib, Cabozantinib, XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin). In another embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441, Tarceva (Erlotinib, OSI-774), CUDC-101 and WZ4002. In another embodiment, the therapeutic agent for combination is a c-Fms and/or c-Kit inhibitor as described in US Patent Application Publication Nos. 2009/0076046 and 2011/0112127, which are incorporated herein by reference in their entirety and for all purposes. In one embodiment, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In some embodiments, a bromodomain modulator, particularly a compound of any of Formulae (I) or (II); or a pharmaceutically acceptable salt, a solvate, a tautomer, an isomer, or a deuterated analog of Formulae (I) or (II); or any of the compounds in Table I, may be administered simultaneously, sequentially or separately in combination with one or more agents as described above.

In another embodiment, the present disclosure provides a composition, e.g., a pharmaceutical composition comprising a compound of Formulae (I) or (II); or a pharmaceutically acceptable salt, a solvate, a tautomer, an isomer, or a deuterated analog of Formulae (I) or (II); any of the compounds in Table I, or any of the pharmaceutical compositions thereof described herein, and one or more other therapeutic agents selected from the group consisting of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxycamptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; xviii) a c-Kit mutant inhibitor, xix) an EGFR inhibitor, or xx) an epigenetic modulator. In further embodiments, a bromodomain modulator, particularly a compound of any of Formulae (I) or (II); or a pharmaceutically acceptable salt, a solvate, a tautomer, an isomer, or a deuterated analog of Formulae (I) or (II); or any of the compounds in Table I, may be administered simultaneously, sequentially or separately in combination with one or more agents as described above.

Epigenetic modulators include DNA methylating agents and agents that modulate posttranslational modification of histones and/or proteins by the activity of chromatin modifiers. Non-limiting examples of Epigenetic modulators include:
(a) DNA methyltransferases (for example, azacytidine, decitabine or zebularine);
(b) histone and protein methyltransferases, including, but not limited to, DOT1L inhibitors such as EPZ004777 (7-[5-Deoxy-5-[[3-[[[[4-(1,1-dimethylethyl)phenyl]

amino]carbonyl]amino]propyl](1-methylethy)amino]-β-D-ribofuranosyl]-7H-pyrrolo[2,3-d]pyrimidin-4-amine), EZH1 inhibitors, EZH2 inhibitors or EPX5687;
(c) histone demethylases;
(d) histone deacetylase inhibitors (HDAC inhibitors) including, but not limited to, vorinostat, romidepsin, chidamide, panobinostat, belinostat, valproic acid, mocetinostat, abexinostat, entinostat, resminostat, givinostat, or quisinostat;
(e) histone acetyltransferase inhibitors (also referred to as HAT inhibitors) including, but not limited to, C-646, (4-[4-[[5-(4,5-Dimethyl-2-nitrophenyl)-2-furanyl]methylene]-4,5-dihydro-3-methyl-5-oxo-1H-pyrazol-1-yl]benzoic acida), CPTH2 (cyclopentylidene-[4-(4'-chlorophenyl)thiazol-2-yl]hydrazine), CTPB (N-(4-chloro-3-trifluoromethyl-phenyl)-2-ethoxy-6-pentadecyl-benzamide), garcinol ((1R,5R,7R)-3-(3,4-Dihydroxybenzyol)-4-hydroxy-8,8-dimethyl-1,7-bis(3-methyl-2-buten-1-yl)-5-[(2S)-5-methyl-2-(1-methylethenyl)-4-hexen-1-yl]bicyclo[3.3.1]non-3-ene-2,9-dione), anacardic acid, EML 425 (5-[(4-hydroxy-2,6-dimethylphenyl)methylene]-1,3-bis(phenylmethyl)-2,4,6(1H,3H,5H)-pyrimidinetrione), ISOX DUAL ([3-[4-[2-[5-(Dimethyl-1,2-oxazol-4-yl)-1-[2-(morpholin-4-yl)ethyl]-1H-1,3-benzodiazol-2-yl]ethyl]phenoxy]propyl]dimethylamine), L002 (4-[O-[(4-methoxyphenyl)sulfonyl]oxime]-2,6-dimethyl-2,5-cyclohexadiene-1,4-dione), NU 9056 (5-(1,2-thiazol-5-yldisulfanyl)-1,2-thiazole), SI-2 hydrochloride (1-(2-pyridinyl)ethanone 2-(1-methyl-1H-benzimidazol-2-yl)hydrazone hydrochloride); or
(f) other chromatin remodelers.

In another embodiment, the epigenetic modulator is vorinostat, romidepsin, belinostat,or panobinostat.

In some embodiments, the present disclosure provides methods for treating a disease or condition mediated by bromodomain, including any mutations thereof, by administering to a subject an effective amount of a composition as described herein, which includes any one or more compound(s) as described herein in combination with one or more other therapeutic agents as described herein. In other embodiments, the present disclosure provides methods for treating a disease or condition mediated by bromodomain protein or mutant bromodomain protein, including any mutations thereof, by administering to a subject an effective amount of a composition as described herein, which includes any one or more compound(s) as described herein in combination with one or more other suitable therapies for treating the disease or condition. In one embodiment, the present disclosure provides methods for treating a cancer mediated by bromodomain or mutant bromodomain by administering to the subject an effective amount of a composition including any one or more compound(s) as described herein. In one embodiment, the present disclosure provides methods for treating a cancer mediated by bromodomain by administering to the subject an effective amount of a composition including any one or more compound(s) as described herein in combination with one or more suitable anticancer therapies, such as one or more chemotherapeutic drugs or agents as described herein.

In some embodiments, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one aspect, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer. The compounds can be administered simultaneously or sequentially.

In some embodiments, the present disclosure provides a composition, e.g., a pharmaceutical composition comprising a compound of Formulae (I) or (II), any of the compounds in Table I, or a pharmaceutically acceptable salt, a solvate, a tautomer, an isomer, or a deuterated analog of Formulae (I) or (II); or any of the compounds in Table I, in combination with a FMS inhibitor, such as quizartinib or pexidartinib.

In one embodiment, the present disclosure provides methods for treating a disease or condition mediated by bromodomain or mutant bromodomain protein, by administering to the subject an effective amount a compound of Formulae (I) or (II), any of the compounds in Table I, or a pharmaceutically acceptable salt, a solvate, a tautomer, an isomer, or a deuterated analog of Formulae (I) or (II); or any of the compounds in Table I, in combination quizartinib for treating the disease or condition.

In some embodiments, the disclosure provides a method of treating a subject suffering from a disease or condition described in this disclosure, said method comprising administering to the subject an effective amount of Formulae (I) or (II), any of the compounds in Table I, or a pharmaceutically acceptable salt, a solvate, a tautomer, an isomer, or a deuterated analog of Formulae (I) or (II); or any of the compounds in Table I, in combination with a mutant c-Kit protein kinase inhibitor. In another embodiment, the mutant c-Kit protein kinase inhibitor is selected from (2-phenyl-1H-pyrrolo[2,3-b]pyridin-5-yl)-(3-pyridyl)methanol, (2-phenyl-1H-pyrrolo[2,3-b]pyridin-5-yl)-(3-pyridyl) methanone, N-(3-carbamoylphenyl)-2-phenyl-1H-pyrrolo[2,3-b]pyridine-5-carboxamide, 2-phenyl-N-(1H-pyrazol-3-yl)-1H-pyrrolo[2,3-b]pyridine-5-carboxamide, 4-bromo-N-(2-phenyl-1H-pyrrolo[2,3-b]pyridin-5-yl)-1H-pyrazole-5-carboxamide, ethyl 3-[(2-phenyl-1H-pyrrolo[2,3-b]pyridin-5-yl)carbamoylamino]propanoate, 3,4-dimethyl-N-(2-phenyl-1H-pyrrolo[2,3-b]pyridin-5-yl)-1H-pyrazole-5-carboxamide, 4-methyl-3-phenyl-N-(2-phenyl-1H-pyrrolo[2,3-b]pyridin-5-yl)-1H-pyrazole-5-carboxamide, 3-cyclopropyl-N-(2-phenyl-1H-pyrrolo[2,3-b]pyridin-5-yl)-1H-pyrazole-5-carboxamide, 5-fluoro-N-(2-phenyl-1H-pyrrolo[2,3-b]pyridin-5-yl)-1H-indazole-3-carboxamide, N-(2-phenyl-1H-pyrrolo[2,3-b]pyridin-5-yl)pyrimidine-4-carboxamide, 3-fluoro-N-(2-phenyl-1H-pyrrolo[2,3-b]pyridin-5-yl)pyridine-2-carboxamide, 3,5-dimethyl-N-(2-phenyl-1H-pyrrolo[2,3-b]pyridin-5-yl)isoxazole-4-carboxamide, N-(2-phenyl-1H-pyrrolo[2,3-b]pyridin-5-yl)pyridazine-3-carboxamide, N-(2-phenyl-1H-pyrrolo[2,3-b]pyridin-5-yl)-2H-triazole-4-carboxamide, 3-methyl-N-(2-phenyl-1H-pyrrolo[2,3-b]pyridin-5-yl)pyridine-2-carboxamide, 4,5-dimethyl-N-(2-phenyl-1H-pyrrolo[2,3-b]pyridin-5-yl)isoxazole-3-carboxamide or N-(2-phenyl-1H- pyrrolo[2,3-b]pyridin-5-yl)-1H-pyrazole-4-sulfonamide. In another embodiment, the compound of Formulae (I) or (II), any of the compounds in Table I, or a pharmaceutically acceptable salt, a solvate, a tautomer, an isomer, or a deuterated analog of Formulae (I) or (II); or any of the compounds in Table I, is combined with any of the mutant c-Kit mutant inhibitiors described in this specification for treating GIST—which includes, without limitation, 1$^{st}$ line, 2$^{nd}$ line and neoadjuvant GIST.

In some embodiments, the present disclosure provides a composition, e.g., a pharmaceutical composition comprising at least one pharmaceutically acceptable carrier or excipient and any of one of the compounds in Table II, or a pharmaceutically acceptable salt, a solvate, a tautomer, an isomer, or a deuterated analog of any of the compounds in Table II in combination with a FMS inhibitor, such as quizartinib or pexidartinib. In some embodiments, the present disclosure provides a pharmaceutical composition comprising: any of one of the compounds in Table II, or a pharmaceutically acceptable salt, a solvate, a tautomer, an isomer, or a deuterated analog of any of the compounds in Table II; a pharmaceutically acceptable carrier; and quizartinib.

In some embodiments, the present disclosure provides methods for treating a subject suffering or at risk of a disease or condition mediated by a bromodomain, said method comprising administering to the subject in need thereof an effective amount of any of the compounds according to Table II or a pharmaceutically acceptable salt, a solvate, a tautomer, an isomer, or a deuterated analog of any of one the compounds in Table II, or a composition comprising any of the compounds in Table II or a pharmaceutically acceptable salt, a solvate, a tautomer, an isomer, or a deuterated analog of any of one the compounds in Table II, and a pharmaceutical acceptable excipient or carrier in combination with quizartinib.

In some embodiments, the present disclosure provides methods for treating a subject suffering or at risk of a disease or condition mediated by a bromodomain, said method comprising administering to the subject in need thereof an effective amount of a pharmaceutical composition comprising: any of one of the compounds in Table II, or a pharmaceutically acceptable salt, a solvate, a tautomer, an isomer, or a deuterated analog of any of the compounds in Table II; at least one pharmaceutically acceptable excipient or carrier; and quizartinib.

TABLE II 3,5-dimethyl-4-[1-(1-phenylethyl)-3-(1,3,5-trimethylpyrazol-4-yl)pyrrolo[3,2-b]pyridin-6-yl]isoxazole
3,5-dimethyl-4-[3-oxazol-5-yl-1-(1-phenylethyl)pyrrolo[3,2-b]pyridin-6-yl]isoxazole
3-[6-(3,5-dimethylisoxazol-4-yl)-1-(1-phenylethyl)pyrrolo[3,2-b]pyridin-3-yl]prop-2-yn-1-ol
4-[1-[(3,3-difluorocyclobutyl)methyl]-3-iodo-pyrrolo[3,2-b]pyridin-6-yl]-3,5-dimethyl-isoxazole
4-[1-[(3,3-difluorocyclobutyl)methyl]-3-[1-(difluoromethyl)pyrazol-4-yl]pyrrolo[3,2-b]pyridin-6-yl]-3,5-dimethyl-isoxazole
4-[1-[(3,3-difluorocyclobutyl)methyl]-3-[1-(2,2,2-trifluoroethyl)pyrazol-4-yl]pyrrolo[3,2-b]pyridin-6-yl]-3,5-dimethyl-isoxazole
4-[3-chloro-1-[(4,4-difluorocyclohexyl)methyl]pyrrolo[3,2-b]pyridin-6-yl]-3,5-dimethyl-isoxazole
3-[3-chloro-6-(3,5-dimethylisoxazol-4-yl)pyrrolo[3,2-b]pyridin-1-yl]-3-cyclopropyl-propanenitrile
3-[3-bromo-6-(3,5-dimethylisoxazol-4-yl)pyrrolo[3,2-b]pyridin-1-yl]-3-cyclopropyl-propanenitrile
3-cyclopropyl-3-[6-(3,5-dimethylisoxazol-4-yl)-3-iodo-pyrrolo[3,2-b]pyridin-1-yl]propanenitrile
1-[(4,4-difluorocyclohexyl)methyl]-6-(3,5-dimethyltriazol-4-yl)-3-(1-methylpyrazol-4-yl)pyrrolo[3,2-b]pyridine
1-[(4,4-difluorocyclohexyl)methyl]-6-(3,5-dimethyltriazol-4-yl)-3-[1-(2,2,2-trifluoroethyl)pyrazol-4-yl]pyrrolo[3,2-b]pyridine
1-[(4,4-difluorocyclohexyl)methyl]-6-(6-methoxy-3-pyridyl)pyrrolo[3,2-b]pyridine
1-[(4,4-difluorocyclohexyl)methyl]-6-(6-methyl-3-pyridyl)pyrrolo[3,2-b]pyridine
3-[3-[1-(difluoromethyl)pyrazol-4-yl]-6-(3,5-dimethylisoxazol-4-yl)pyrrolo[3,2-b]pyridin-1-yl]-3-tetrahydropyran-4-yl-propanenitrile
3-cyclopropyl-3-[6-(3,5-dimethylisoxazol-4-yl)-3-[1-(2,2,2-trifluoroethyl)pyrazol-4-yl]pyrrolo[3,2-b]pyridin-1-yl]propanenitrile
3-cyclopropyl-3-[6-(3,5-dimethylisoxazol-4-yl)-3-(1-methylpyrazol-4-yl)pyrrolo[3,2-b]pyridin-1-yl]propanenitrile
4-[1-benzyl-3-[1-(2,2,2-trifluoroethyl)pyrazol-4-yl]pyrrolo[3,2-b]pyridin-6-yl]-3,5-dimethyl-isoxazole
4-(1-benzyl-3-iodo-pyrrolo[3,2-b]pyridin-6-yl)-3,5-dimethyl-isoxazole
4-[3-iodo-1-(pyrimidin-2-ylmethyl)pyrrolo[3,2-b]pyridin-6-yl]-3,5-dimethyl-isoxazole
3,5-dimethyl-4-[1-[1-(2-pyridyl)ethyl]-3-[1-(2,2,2-trifluoroethyl)pyrazol-4-yl]pyrrolo[3,2-b]pyridin-6-yl]isoxazole
3,5-dimethyl-4-[1-[(1,4,4-trifluorocyclohexyl)methyl]-3-[1-(2,2,2-trifluoroethyl)pyrazol-4-yl]pyrrolo[3,2-b]pyridin-6-yl]isoxazole
5-[3-(chloromethyl)-5-methyl-1,2,4-triazol-4-yl]-1H-pyrrolo[2,3-b]pyridine
tert-butyl N-[4-[1-[(4,4-difluorocyclohexyl)methyl]pyrrolo[3,2-b]pyridin-6-yl]-5-methyl-isoxazol-3-yl]carbamate
4-[1-[(4,4-difluorocyclohexyl)methyl]-6-(3,5-dimethylisoxazol-4-yl)pyrrolo[3,2-b]pyridin-3-yl]benzoic acid
3,5-dimethyl-4-[3-(1-methylpyrazol-4-yl)-1-(pyrimidin-2-ylmethyl)pyrrolo[3,2-b]pyridin-6-yl]isoxazole
4-[1-benzyl-3-[1-(difluoromethyl)pyrazol-4-yl]pyrrolo [3,2-b]pyridin-6-yl]-3,5-dimethyl-isoxazole
4-[1-benzyl-3-(1-methylpyrazol-4-yl)pyrrolo [3,2-b]pyridin-6-yl]-3,5-dimethyl-isoxazole
4-[1-[(4,4-difluorocyclohexyl)methyl]pyrrolo[3,2-b]pyridin-6-yl]-3-methyl-isoxazol-5-amine
4-[1-[(4,4-difluorocyclohexyl)methyl]pyrrolo[3,2-b]pyridin-6-yl]-5-methyl-isoxazol-3-amine
methyl 4-[1-[(4,4-difluorocyclohexyl)methyl]-6-(3,5-dimethylisoxazol-4-yl)pyrrolo[3,2-b]pyridin-3-yl]benzoate TABLE II-continued 3-[6-(3,5-dimethylisoxazol-4-yl)-3-(1-methylpyrazol-4-yl)pyrrolo[3,2-b]pyridin-1-yl]-3-phenyl-propanenitrile
3-[6-(3,5-dimethylisoxazol-4-yl)-3-[1-(2,2,2-trifluoroethyl)pyrazol-4-yl]pyrrolo[3,2-b]pyridin-1-yl]-3-phenyl-propanenitrile
4-[3-iodo-1-(2-pyridylmethyl)pyrrolo[3,2-b]pyridin-6-yl]-3,5-dimethyl-isoxazole
4-[1-[dideuterio-(4,4-difluorocyclohexyl)methyl]-3-oxazol-5-yl-pyrrolo[3,2-b]pyridin-6-yl]-3,5-dimethyl-isoxazole
4-[1-[dideuterio-(4,4-difluorocyclohexyl)methyl]-3-(1,3-dimethylpyrazol-4-yl)pyrrolo[3,2-b]pyridin-6-yl]-3,5-dimethyl-isoxazole
4-[1-[dideuterio-(4,4-difluorocyclohexyl)methyl]-3-(1-ethylpyrazol-4-yl)pyrrolo[3,2-b]pyridin-6-yl]-3,5-dimethyl-isoxazole
4-[1-[dideuterio-(4,4-difluorocyclohexyl)methyl]-3-[1-methyl-3-(trifluoromethyl)pyrazol-4-yl]pyrrolo[3,2-b]pyridin-6-yl]-3,5-dimethyl-isoxazole
4-[1-[dideuterio-(4,4-difluorocyclohexyl)methyl]-3-(1,5-dimethylpyrazol-4-yl)pyrrolo[3,2-b]pyridin-6-yl]-3,5-dimethyl-isoxazole
3-[4-[1-[dideuterio-(4,4-difluorocyclohexyl)methyl]-6-(3,5-dimethylisoxazol-4-yl)pyrrolo[3,2-b]pyridin-3-yl]pyrazol-1-yl]propanenitrile
4-[1-[dideuterio-(4,4-difluorocyclohexyl)methyl]-3-(3-pyridyl)pyrrolo[3,2-b]pyridin-6-yl]-3,5-dimethyl-isoxazole
4-[3-(2-cyclopropyl-4-pyridyl)-1-[dideuterio-(4,4-difluorocyclohexyl)methyl]pyrrolo[3,2-b]pyridin-6-yl]-3,5-dimethyl-isoxazole
5-[1-[dideuterio-(4,4-difluorocyclohexyl)methyl]-6-(3,5-dimethylisoxazol-4-yl)pyrrolo[3,2-b]pyridin-3-yl]pyridin-2-ol
4-[1-[dideuterio-(4,4-difluorocyclohexyl)methyl]-3-(6-methoxy-3-pyridyl)pyrrolo[3,2-b]pyridin-6-yl]-3,5-dimethyl-isoxazole The compounds in Table II are disclosed in WO 2014/145051, including methods of how to make these compounds, and the contents of WO 2014/145051 are incorporated herein by reference in its entirety.

In some embodiments, the present disclosure provides a method of treating a cancer as described herein in a subject in need thereof by administering to the subject an effective amount of a compound or a composition including any one or more compound(s) as described herein, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In certain embodiments, the present disclosure provides a method of treating a cancer in a subject in need thereof by administering to the subject an effective amount of a compound as described herein and applying a radiation treatment as described herein either separately or simultaneously. In one embodiment, the present disclosure provides a method for treating a cancer in a subject in need thereof by administering an effective amount of a compound as described herein to the subject followed by a radiation treatment (e.g. x-ray, γ-ray, or electron, proton, neutron, or α particle beam). In another embodiment, the present disclosure provides a method for treating a cancer in a subject in need thereof by applying a radiation treatment (e.g. x-ray, γ-ray, or electron, proton, neutron, or α particle beam) to the subject followed by administering an effective amount of a compound as described herein to the subject. In yet another embodiment, the present disclosure provides a method for treating a cancer in a subject in need thereof by administering a compound as described herein and a radiation therapy (e.g. x-ray, γ-ray, or electron, proton, neutron, or a particle beam) to the subject simultaneously.

In another aspect, the present disclosure provides kits or containers that include a compound of Formulae (I) or (II); or a pharmaceutically acceptable salt, a solvate, a tautomer, an isomer, or a deuterated analog of Formulae (I) or (II);or any of the compounds in Table I, or any of the pharmaceutical compositions thereof described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a bromodomain protein mediated disease or condition; the kit or container disclosed herein may include written instructions for use and/or other indication that the compound or composition is suitable or approved for administration to a mammal, e.g., a human, for a bromodomain-mediated disease or condition; and the compound or composition may be packaged in unit dose or single dose form, e.g., single dose pills, capsules, or the like.

VII. EXAMPLES

The following examples are offered to illustrate, but not to limit the present disclosure.

Compounds within the scope of this disclosure can be synthesized as described below, using a variety of reactions known to the skilled artisan. One skilled in the art will also recognize that alternative methods may be employed to synthesize the target compounds of the present disclosure, and that the approaches described within the body of this document are not exhaustive, but do provide broadly applicable and practical routes to compounds of interest. In some examples, the mass spectrometry result indicated for a compound may have more than one value due to the isotope distribution of an atom in the molecule, such as a compound having a bromo or chloro substituent.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1A

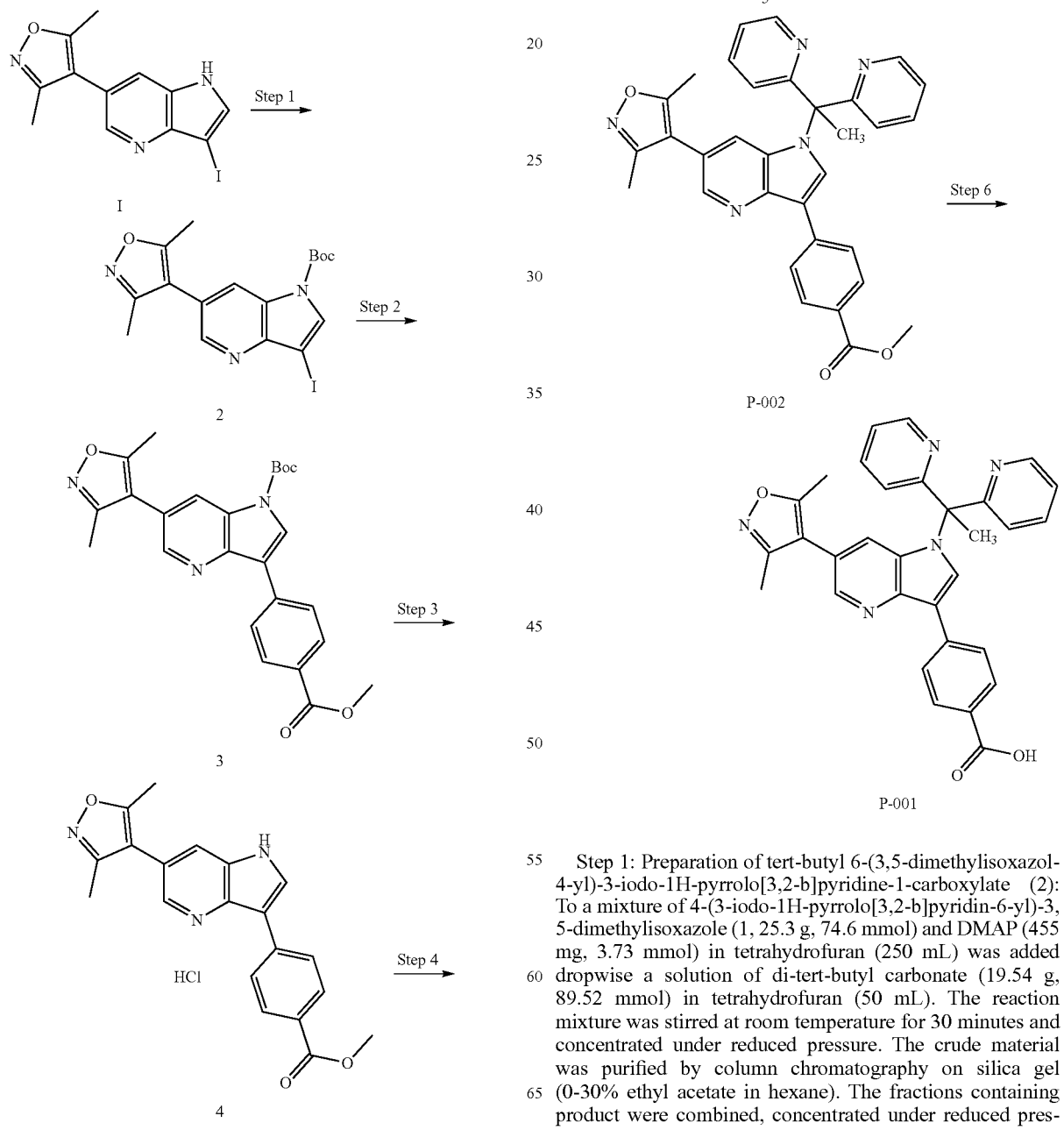

Step 1: Preparation of tert-butyl 6-(3,5-dimethylisoxazol-4-yl)-3-iodo-1H-pyrrolo[3,2-b]pyridine-1-carboxylate (2): To a mixture of 4-(3-iodo-1H-pyrrolo[3,2-b]pyridin-6-yl)-3,5-dimethylisoxazole (1, 25.3 g, 74.6 mmol) and DMAP (455 mg, 3.73 mmol) in tetrahydrofuran (250 mL) was added dropwise a solution of di-tert-butyl carbonate (19.54 g, 89.52 mmol) in tetrahydrofuran (50 mL). The reaction mixture was stirred at room temperature for 30 minutes and concentrated under reduced pressure. The crude material was purified by column chromatography on silica gel (0-30% ethyl acetate in hexane). The fractions containing product were combined, concentrated under reduced pressure, and dried under high vacuum overnight to provide tert-butyl 6-(3,5-dimethylisoxazol-4-yl)-3-iodo-1H-pyrrolo[3,2-b]pyridine-1-carboxylate (2). MS (ESI) [M+H$^+$]$^+$ =440.1.

Step 2: Preparation of tert-butyl 6-(3,5-dimethylisoxazol-4-yl)-3-(4-(methoxycarbonyl)phenyl)-1H-pyrrolo[3,2-b]pyridine-1-carboxylate (3): To a pressure vessel charged with tert-butyl 6-(3,5-dimethylisoxazol-4-yl)-3-iodo-1H-pyrrolo[3,2-b]pyridine-1-carboxylate (2, 15.0 g, 34.15 mmol) and (4-methoxycarbonylphenyl)boronic acid (12.3 g, 68.32 mmol) in toluene (230 mL) and ethanol (70 mL) was added a 2 M aqueous solution of $Na_2CO_3$ (51 mL, 102.5 mmol) followed by addition of [1,1'-bis(diphenylphosphino)ferrocene]dichloropalladium(II) (1.25 g, 1.7 mmol). The resulting mixture was allowed stir under nitrogen for 5 minutes. The vessel was then sealed and heated at 105-110° C. for 2.5 hours. After completion, the reaction mixture was cooled down to room temperature, diluted with dichloromethane (300 mL), and filtered through a pad of celite. The solvents were concentrated under reduced pressure and the residue was poured into a saturated aqueous solution of $NaHCO_3$ (300 mL) and extracted with ethyl acetate (2×200 mL). The combined organic layers were washed with water (2×200 mL) and brine (200 mL), dried over $Na_2SO_4$, filtered and concentrated under reduced pressure. The residue was triturated with $EtOAc/Et_2O$/hexane and the resulting solid was collected by filtration. The solid was washed with the mixture of $EtOAc/Et_2O$ and then dried under high vacuum to provide tert-butyl 6-(3,5-dimethylisoxazol-4-yl)-3-(4-(methoxycarbonyl)phenyl)-1H-pyrrolo[3,2-b]pyridine-1-carboxylate (3). MS (ESI) [M+H$^+$]$^+$=447.48.

Step 3: Preparation of methyl 4-(6-(3,5-dimethylisoxazol-4-yl)-1H-pyrrolo[3,2-b]pyridin-3-yl)benzoate hydrochloride (4): To tert-butyl 6-(3,5-dimethylisoxazol-4-yl)-3-(4-(methoxycarbonyl)phenyl)-1H-pyrrolo[3,2-b]pyridine-1-carboxylate (3, 39.5 g, 88.3 mmol) in $CH_2Cl_2$/MeOH (2:1, 350 mL) was added 4 M HCl in dioxane (220 mL, 88 mmol) at 0° C., and the mixture was allowed to stir at ambient temperature for 2 days. The solid was collected by filtration, washed with cold dichloromethane (150 mL) and with diethylether (3×100 mL), and then dried under high vacuum to provide methyl 4-(6-(3,5-dimethylisoxazol-4-yl)-1H-pyrrolo[3,2-b]pyridin-3-yl)benzoate hydrochloride (4). MS (ESI) [M+H$^+$]$^+$=347.12.

Step 4: Preparation of methyl 4-(1-(di(pyridin-2-yl)methyl)-6-(3,5-dimethylisoxazol-4-yl)-1H-pyrrolo[3,2-b]pyridin-3-yl)benzoate (5): To methyl 4-[6-(3,5-dimethylisoxazol-4-yl)-1H-pyrrolo[3,2-b]pyridin-3-yl]benzoate hydrochloride (4, 1.33 g, 3.47 mmol) in THF (20 mL) was added cesium carbonate (3.39 g, 10.4 mmol) and 2-[bromo(2-pyridyl)methyl]pyridine (1.04 g, 4.16 mmol). The mixture was heated and allowed to stir at 70° C. for 24 hours. LC-MS showed that the starting material (methyl 4-(6-(3,5-dimethylisoxazol-4-yl)-1H-pyrrolo[3,2-b]pyridin-3-yl)benzoate) was still present. Then, additional 2-[bromo(2-pyridyl)methyl]pyridine (500 mg, 2.01 mmol) was added into the reaction mixture and allowed to stir at 70° C. for another 24 hours. The reaction mixture was poured into water and extracted with ethyl acetate. The organic layer was washed with water and brine, dried over $MgSO_4$, and filtered. The volatiles were removed under vacuum to provide crude material that was purified by silica gel column chromatography (0-80% ethyl acetate in dichloromethane). The fractions containing product were combined and concentrated under reduced pressure and dried under high vacuum overnight to provide methyl 4-(1-(di(pyridin-2-yl)methyl)-6-(3,5-dimethylisoxazol-4-yl)-1H-pyrrolo[3,2-b]pyridin-3-yl)benzoate (5). MS (ESI) [M+H$^+$]$^+$=515.56.

Step 5: Preparation of methyl 4-(1-(1,1-di(pyridin-2-yl)ethyl)-6-(3,5-dimethylisoxazol-4-yl)-1H-pyrrolo[3,2-b]pyridin-3-yl)benzoate (P-002): To methyl 4-[1-[bis(2-pyridyl)methyl]-6-(3,5-dimethylisoxazol-4-yl)pyrrolo[3,2-b]pyridin-3-yl]benzoate (5, 0.36 g, 0.7 mmol) in tetrahydrofuran (15 mL) was added sodium hydride (60% in mineral oil, 0.03 g, 0.8 mmol). The mixture was allowed to stir at room temperature for 10 minutes. Then, iodomethane (0.5 g, 3.5 mmol) was added and the reaction mixture was allowed to stir at room temperature for 20 hours. The reaction mixture was poured into water and extracted with ethyl acetate. The organic layer was washed with water and brine, dried over $MgSO_4$, and filtered. The volatiles were removed under vacuum. The crude product was purified by silica gel column chromatography (0-100% ethyl acetate in dichloromethane). The fractions containing product were combined and concentrated under reduced pressure and dried under high vacuum overnight to provide methyl 4-(1-(1,1-di(pyridin-2-yl)ethyl)-6-(3,5-dimethylisoxazol-4-yl)-1H-pyrrolo[3,2-b]pyridin-3-yl)benzoate (P-002). MS (ESI) [M+H$^+$]$^+$=529.59.

Step 6: Preparation of 4-(1-(1,1-di(pyridin-2-yl)ethyl)-6-(3,5-dimethylisoxazol-4-yl)-1H-pyrrolo[3,2-b]pyridin-3-yl)benzoic acid (P-001): To methyl 4-[1-[1,1-bis(2-pyridyl)ethyl]-6-(3,5-dimethylisoxazol-4-yl)pyrrolo[3,2-b]pyridin-3-yl]benzoate (P-002, 180 mg, 0.34 mmol) in THF (15 mL) was added 1 M lithium hydroxide (7.5 mL) in water. The reaction mixture was heated and allowed to stir at 50° C. for 20 hours. The reaction mixture was poured into water along with 5 mL of acetic acid and extracted with ethyl acetate. The organic layer was washed with water and brine, dried over $MgSO_4$, and filtered. After the volatiles were removed, the residue was dissolved in acetonitrile after heating to reflux. After cooling to room temperature the solution was allowed to sit in the refrigerator overnight. The product was collected by filtration to provide 4-(1-(1,1-di(pyridin-2-yl)ethyl)-6-(3,5-dimethylisoxazol-4-yl)-1H-pyrrolo[3,2-b]pyridin-3-yl)benzoic acid (P-001). MS (ESI) [M+H$^+$]$^+$=515.56.

Alternatively, P-001 can be synthesized according to Example 1B:

Scheme 1B

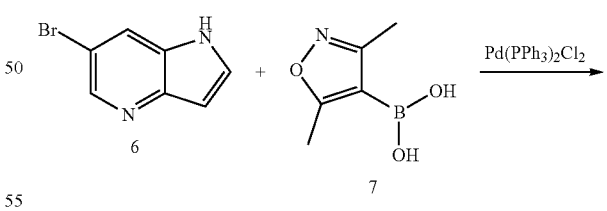

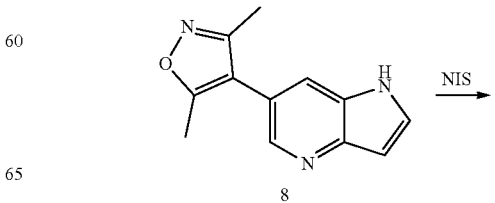

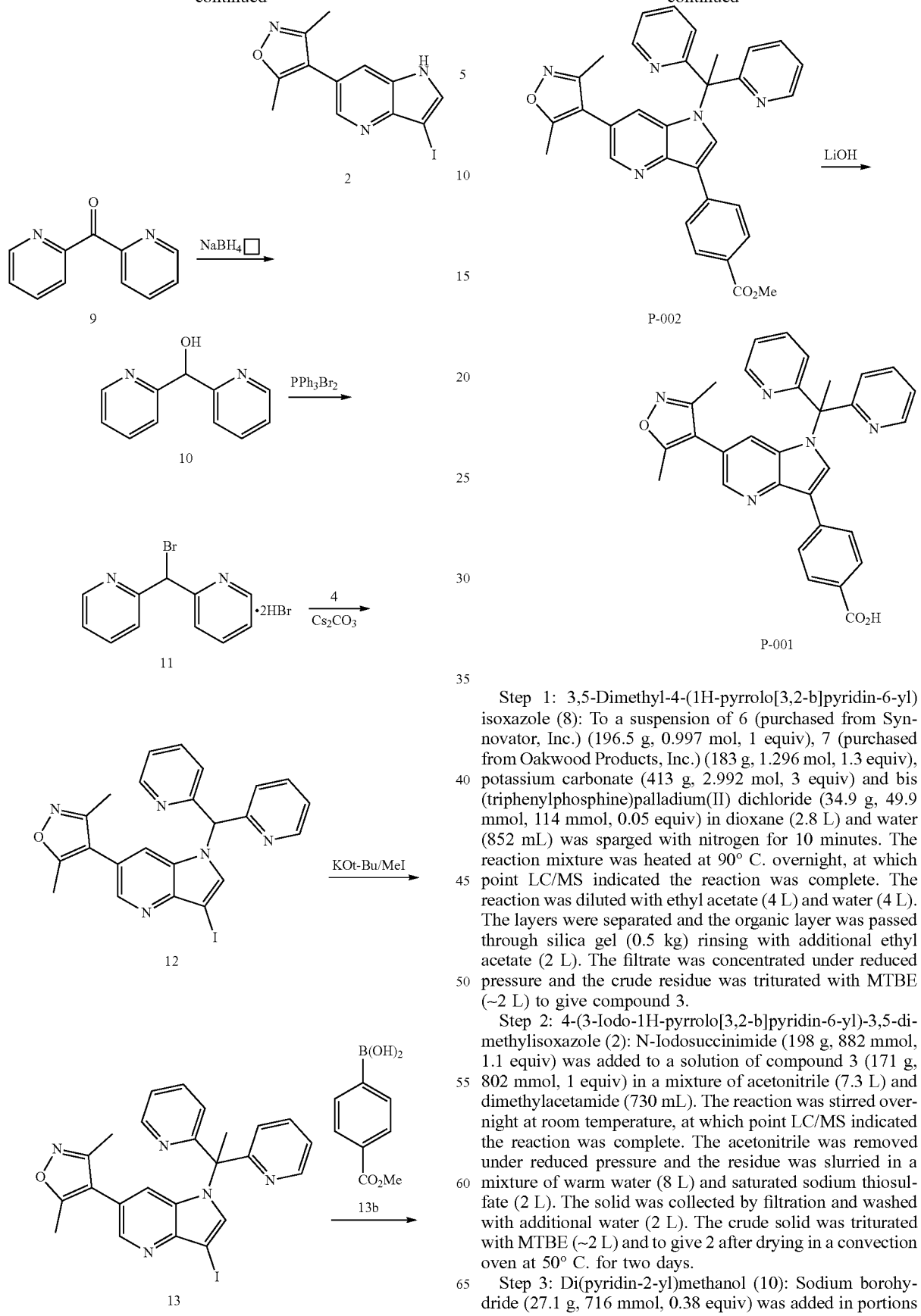

Step 1: 3,5-Dimethyl-4-(1H-pyrrolo[3,2-b]pyridin-6-yl)isoxazole (8): To a suspension of 6 (purchased from Synnovator, Inc.) (196.5 g, 0.997 mol, 1 equiv), 7 (purchased from Oakwood Products, Inc.) (183 g, 1.296 mol, 1.3 equiv), potassium carbonate (413 g, 2.992 mol, 3 equiv) and bis(triphenylphosphine)palladium(II) dichloride (34.9 g, 49.9 mmol, 114 mmol, 0.05 equiv) in dioxane (2.8 L) and water (852 mL) was sparged with nitrogen for 10 minutes. The reaction mixture was heated at 90° C. overnight, at which point LC/MS indicated the reaction was complete. The reaction was diluted with ethyl acetate (4 L) and water (4 L). The layers were separated and the organic layer was passed through silica gel (0.5 kg) rinsing with additional ethyl acetate (2 L). The filtrate was concentrated under reduced pressure and the crude residue was triturated with MTBE (~2 L) to give compound 3.

Step 2: 4-(3-Iodo-1H-pyrrolo[3,2-b]pyridin-6-yl)-3,5-dimethylisoxazole (2): N-Iodosuccinimide (198 g, 882 mmol, 1.1 equiv) was added to a solution of compound 3 (171 g, 802 mmol, 1 equiv) in a mixture of acetonitrile (7.3 L) and dimethylacetamide (730 mL). The reaction was stirred overnight at room temperature, at which point LC/MS indicated the reaction was complete. The acetonitrile was removed under reduced pressure and the residue was slurried in a mixture of warm water (8 L) and saturated sodium thiosulfate (2 L). The solid was collected by filtration and washed with additional water (2 L). The crude solid was triturated with MTBE (~2 L) and to give 2 after drying in a convection oven at 50° C. for two days.

Step 3: Di(pyridin-2-yl)methanol (10): Sodium borohydride (27.1 g, 716 mmol, 0.38 equiv) was added in portions to a solution of 9 (purchased from RennoteTech Co., LTD)

(350. g, 1900 mmol, 1 equiv) in methanol (7 L) at 0° C. The reaction was allowed to stir for 1.5 hours at which point LCMS indicated full consumption of 9. The solution was concentrated under reduced pressure. The residue was dissolved in 1N hydrochloric acid (2.56 L). The pH was adjusted to ~8 with solid sodium bicarbonate (344 g). The solution was extracted twice with ethyl acetate (2×3 L). The combined organic layers were concentrated under reduced pressure to give 10 which was used subsequently in the next step.

Step 4: 2,2'-(Bromomethylene)dipyridine dihydrobromic acid (11): Triphenylphosphine dibromide (322.5 g, 764 mmol, 2 equiv) was added in portions to a solution of 9 (71.2 g, 382 mmol, 1 equiv) in dichloromethane (1.6 L) at room temperature. The reaction was allowed to stir at room temperature overnight. The suspension was filtered under nitrogen and washed with dichloromethane (2×100 mL). The solid was dried under vacuum oven at 40° C. for 3 hours to give 11. The solid was hygroscopic and was not left exposed to air.

Step 5: 4-(1-(Di(pyridin-2-yl)methyl)-3-iodo-1H-pyrrolo[3,2-b]pyridin-6-yl)-3,5-dimethylisoxazole (12): 11 (178.4 g, 435 mmol, 1.58 equiv) was suspended in a saturated solution of sodium bicarbonate (2 L) and extracted with dichloromethane (3×1 L). The combined organic layers were concentrated under reduced pressure to give the free base of 11 (108.2 g, 435 mmol, 1.58 equiv). Free base of 11 (108.2 g, 435 mmol, 1.58 equiv), 2 (93.5 g, 276 mmol, 1 equiv) and cesium carbonate (208 g, 638 mmol, 2.3 equiv) were dissolved in THF (3 L) and refluxed overnight. The solution was diluted with saturated brine (3 L). The organic layer was separated and concentrated under reduced pressure. The residue was purified twice over silica gel (2×700 g), eluting each time with a gradient of 0 to 100% ethyl acetate in dichloromethane. The material was triturated with MTBE (500 mL) to 12.

Step 6: 4-(1-(1,1-Di(pyridin-2-yl)ethyl)-3-iodo-1H-pyrrolo[3,2-b]pyridin-6-yl)-3,5-dimethylisoxazole (13): Potassium tert-butoxide (29.4 g, 239 mmol, 1.2 equiv) was added in portions to a solution of 12 (101.0 g, 199 mmol, 1 equiv) and iodomethane (37.2 mL, 597 mmol, 3 equiv) in anhydrous THF. The reaction was allowed to stir at room temperature overnight. The solution was quenched with saturated brine (2 L). The organic layer was separated and concentrated under reduced pressure. The residue was partially purified over silica gel (1 kg) eluting with a gradient of 0 to 40% ethyl acetate in dichloromethane. The mixed fractions were purified in two batches on the same AnaLogix column (220 g) eluting each time with 0 to 50% ethyl acetate in dichloromethane. Clean fractions were combined to give 13.

Step 7: Methyl 4-(1-(1,1-di(pyridin-2-yl)ethyl)-6-(3,5-dimethylisoxazol-4-yl)-1H-pyrrolo[3,2-b]pyridin-3-yl)benzoate (P-002): A mixture of 13 (73.4 g, 141 mmol, 1 equiv), and 13b (purchased from Angene International Limited) (50.7 g, 282 mmol, 2 equiv), and potassium carbonate (58.3 g, 422 mmol, 3 equiv) in dioxane (730 mL) and water (245 mL) were sparged with nitrogen for 10 minutes. [1,1'-Bis(diphenylphosphino)ferrocene]dichloropalladium(II) (6.2 g, 8.4 mmol, 0.06 equiv) was added and the reaction was heated to 80° C. for 1.5 hours. After cooling to room temperature, the solution was diluted with THF (500 mL) and filtered through Celite (95 g), washing with additional THF (600 mL). The Celite pad was slurried in dichloromethane (1 L) and filtered. The two filtrates were combined and concentrated under reduced pressure. The residue was purified over silica gel (1 kg), eluting with a gradient of 0 to 100% ethyl acetate in heptanes. The mixed fractions were combined and triturated with MTBE (200 mL). The filtrate was concentrated under reduced pressure and purified on an AnaLogix column (220 g), eluting with a gradient of 0 to 50% ethyl acetate in heptanes. All clean material was combined to give P-002.

Step 8: 4-(1-(1,1-Di(pyridin-2-yl)ethyl)-6-(3,5-dimethylisoxazol-4-yl)-1H-pyrrolo[3,2-b]pyridin-3-yl)benzoic acid (P-001): A solution of P-002 (79.2 g, 150 mmol, 1 equiv) and 2M lithium hydroxide (1.125 L, 2250 mmol, 15 equiv) in THF (2.2 L) were heated to 55° C. overnight. The solution was diluted with saturated brine (2 L). The pH was adjusted to ~5 with 1 N hydrochloric acid (1.6 L). The solution was extracted with ethyl acetate (2.2 L). The organic layer was separated, dried over sodium sulfate, and concentrated under reduced pressure. The residue was dissolved in dichloromethane (1 L) and filtered to remove insoluble particles. The filtrate was diluted with acetonitrile (1 L) and concentrated to a thick slurry. The suspension was filtered. The filtrate was treated repeatedly in the same fashion until no isolable material remained. All solids were combined to give P-001.

Example 2

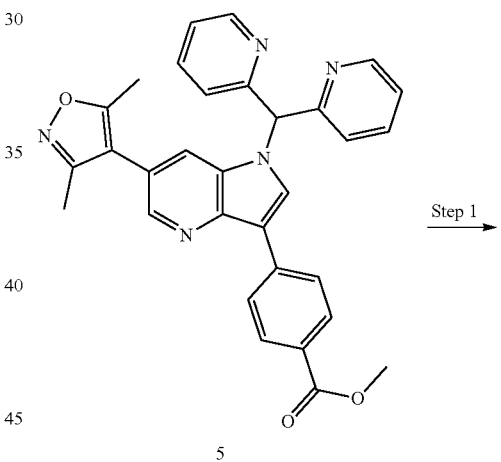

5

Step 1 →

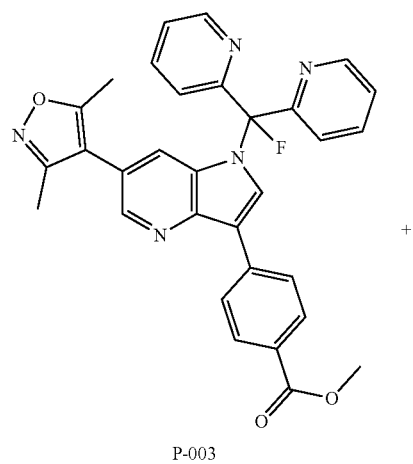

P-003

+

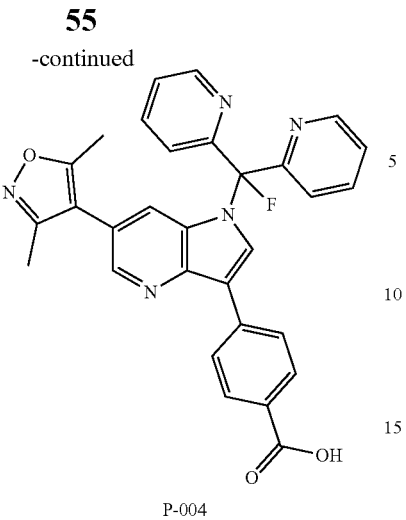

P-004

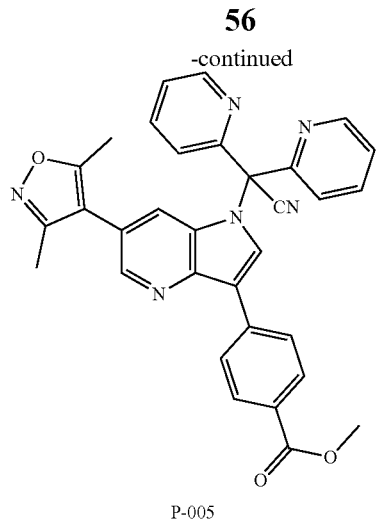

P-005

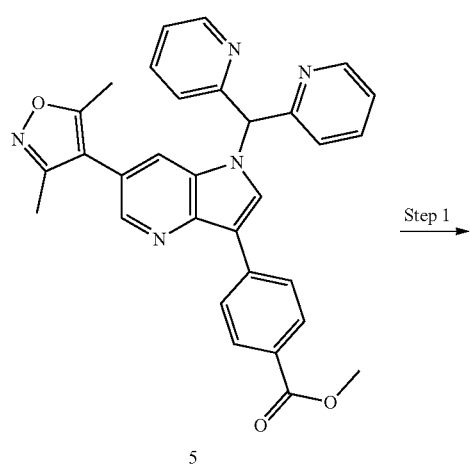

P-006

Step 1—Preparation of methyl 4-(6-(3,5-dimethylisoxazol-4-yl)-1-(fluorodi(pyridin-2-yl)methyl)-1H-pyrrolo[3,2-b]pyridin-3-yl)benzoate (P-003) and 4-(6-(3,5-dimethylisoxazol-4-yl)-1-(fluorodi(pyridin-2-yl)methyl)-1H-pyrrolo[3,2-b]pyridin-3-yl)benzoic acid (P-004): In a vial charged with methyl 4-[1-[bis(2-pyridyl)methyl]-6-(3,5-dimethylisoxazol-4-yl)pyrrolo[3,2-b]pyridin-3-yl]benzoate (5, 0.09 g, 0.17 mmol) and potassium hydroxide (150 mg, 2.68 mmol) was added N,N-dimethylformamide (2 mL). The mixture was allowed to stir at room temperature for 1 hour and a solution of N-fluorobenzenesulfonimide (100 mg, 0.315.34 mmol) in 1 mL N,N-dimethylformamide was added. The mixture was allowed to stir at room temperature for 2 hours. The reaction mixture was poured into water along with 5 mL of acetic acid, and then extracted with ethyl acetate. The organic layer was washed with water and brine, dried over $MgSO_4$, and filtered. The crude product was purified by preparative HPLC. The pure fractions were combined and dried on the lyophilizer to provide methyl 4-(6-(3,5-dimethylisoxazol-4-yl)-1-(fluorodi(pyridin-2-yl)methyl)-1H-pyrrolo[3,2-b]pyridin-3-yl)benzoate (P-003, 6 mg, 7%), MS (ESI) $[M+H^+]^-$=533.55; and 4-(6-(3,5-dimethylisoxazol-4-yl)-1-(fluorodi(pyridin-2-yl)methyl)-1H-pyrrolo[3,2-b]pyridin-3-yl)benzoic acid (P-004), MS (ESI) $[M+H^+]^+$=519.52.

Example 3

Step 1—Preparation of methyl 4-[1-[cyano-bis(2-pyridyl)methyl]-6-(3,5-dimethylisoxazol-4-yl)pyrrolo[3,2-b]pyridin-3-yl]benzoate (P-005): To a vial charged with methyl 4-[1-[bis(2-pyridyl)methyl]-6-(3,5-dimethylisoxazol-4-yl)pyrrolo[3,2-b]pyridin-3-yl]benzoate (5, 0.08 g, 0.16 mmol) and potassium hydroxide (0.15 g, 2.67 mmol) was added N,N-dimethylformamide (5 mL) and the mixture was allowed to stir at room temperature for 10 minutes. Then, a solution of phenyl cyanate (20%, 0.4 g, 0.67 mmol) in dichloromethane was added to the reaction and allowed to stir at room temperature for 1 hour. LC-MS showed the reaction was not completed, so additional phenyl cyanate (20%, 0.3 gram, 0.502 mmol) was added. The reaction mixture was allowed to stir at room temperature for another 2 hours. The reaction mixture was poured into water along with 5 mL of acetic acid and extracted with ethyl acetate. The organic layer was washed with water and brine, dried over $MgSO_4$, and filtered. The crude material was purified by silica gel column chromatography (0-80% ethyl acetate in hexane). The fractions containing product were combined and concentrated under reduced pressure and dried under high vacuum overnight to provide methyl 4-[1-[cyano-bis(2-pyridyl)methyl]-6-(3,5-dimethylisoxazol-4-yl)pyrrolo[3,2-b]pyridin-3-yl]benzoate (P-005). MS (ESI) $[M+H^+]^+$= 540.57.

Step 2—Preparation of 4-[1-[cyano-bis(2-pyridyl)methyl]-6-(3,5-dimethylisoxazol-4-yl)pyrrolo[3,2-b]pyridin-3-yl]benzoic acid (P-006): The product (P-006, 4-[1-[cyano-bis(2-pyridyl)methyl]-6-(3,5-dimethylisoxazol-4-yl)

pyrrolo[3,2-b]pyridin-3-yl]benzoic acid) was prepared as depicted in Step 6 of Example 1 using the appropriate starting materials. MS (ESI) [M+H⁺]⁺=526.54.

Another embodiment of this disclosure relates to a compound useful for a synthesis of the compound of claim 1, having one of the following formulae:

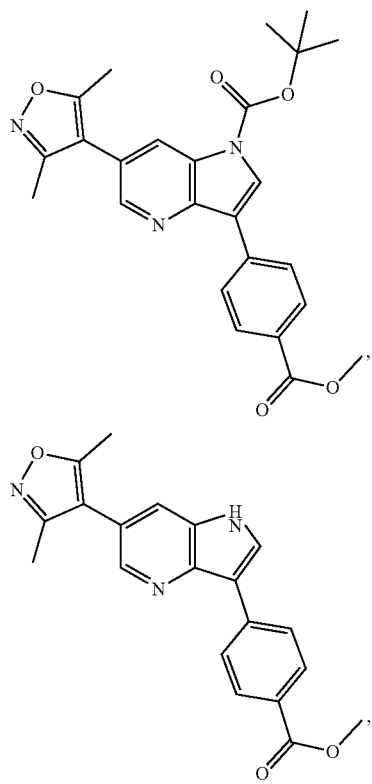

or a pharmaceutically acceptable salt, a solvate, a tautomer, an isomer, or a deuterated analog thereof.

Example 4

Comparison of Rat PK between Compound P-001 and Compound Z

Rat PK data was determined using a cassette dosing format with 5 compounds administered to each of three rats for IV and three rats for PO. The IV dose was 1 mg/kg for each compound in 8.75% solutol, 8.75% ethanol, 12.5% DMSO and 70% water by volume. The PO dose was 2 mg/kg for each compound in 1% methylcellulose in water, 10% DMSO by volume. Plasma IV samples were collected at 15 min, 30 min, 1 hr, 2 hrs, 4 hrs, 8 hrs, and 24 hrs. Plasma PO samples were collected at 30 min, 1 hr, 2 hrs, 4 hrs, 8 hrs, and 24 hrs. Plasma drug concentrations were determined by LC/MS/MS after standard curve calibration for each test article. Dosing solutions were also analyzed for test article and used to calculate the administered dose. The PK parameters were calculated using WinNonLin (v 6.3, Phoenix 64, Pharsight) using a noncompartmental model.

Tables 1 and 2 show comparative data for both intravenous (IV) and peroral (PO) administration in rat for Compound P-001 of this disclosure and a similar structural compound disclosed in the WO 2014/145051, Compound Z. Values are reported as the Mean with the Standard Error (SE) in parentheses. The data demonstate a dramatic improvement in rat PK for Compound P-001 when compared to the rat PK for Compound Z.

TABLE 1

| Intravenous (IV) Administration in Rat | | | | | |
|---|---|---|---|---|---|
| Compound | Dose (mg/kg) | $T_{1/2}$ (hr) | $T_{max}$ (hr) | $C_{max}$ (ng/mL) | AUC (hr*ng/mL) |
| 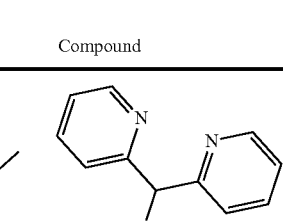 Compound Z | 1.56 | 1.31 (0.15) | 0.5 (0) | 80 (11) | 125 (15) |

TABLE 1-continued
| | Intravenous (IV) Administration in Rat | | | | |
|---|---|---|---|---|---|
| Compound | Dose (mg/kg) | $T_{1/2}$ (hr) | $T_{max}$ (hr) | $C_{max}$ (ng/mL) | AUC (hr*ng/mL) |
| 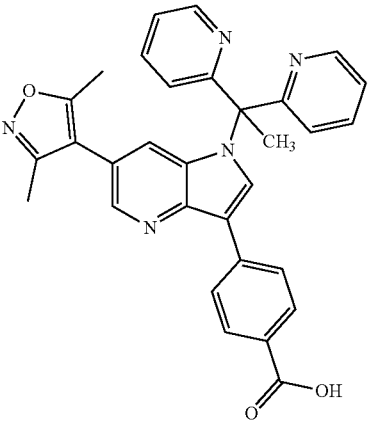 Compound P-001 | 1.27 | 4.13 (0.74) | 0.67 (0.17) | 1212 (118) | 7670 (451) |
TABLE 2
| | Peroral (PO) Administration in Rat | | | |
|---|---|---|---|---|
| Compound | AUC (hr*ng/mL) | Vss (L/Kg) | Cl (mL/min/Kg) | % F |
| 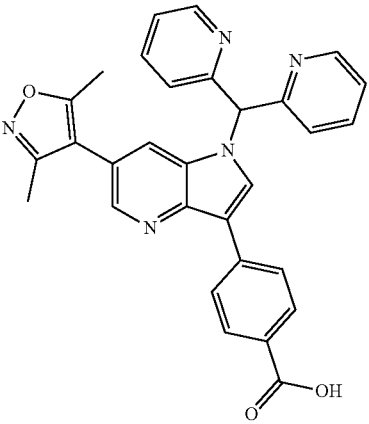 Compound Z | 125 (15) | 1.061 (0.109) | 36 (4) | 17 |

TABLE 2-continued

| | Peroral (PO) Administration in Rat | | | |
|---|---|---|---|---|
| Compound | AUC (hr*ng/mL) | Vss (L/Kg) | Cl (mL/min/Kg) | % F |
| 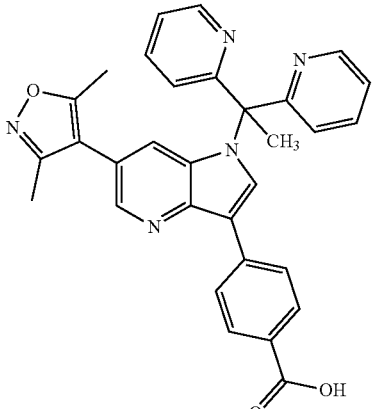<br>Compound P-001 | 7670 (451) | 0.469 (0.015) | 3 (0) | 103 |

Example 5

Efficacy Comparison Between Compound P-001 and Compound Z Using IPC298 Xenograft Model Treatment: The treatments started on Day 11 after tumor inoculation when the mean tumor size reached approximately 150 mm$^3$. Mice were randomized into 10 study groups and each group consisted of 8 mice. The test articles were administrated to the tumor-bearing mice according to predetermined treatment regimen as shown in Table 3.

TABLE 3

| | | Treatment Schedule | | |
|---|---|---|---|---|
| Group | n* | Treatment | Dosage** (mg/kg) | Route/schedule |
| 1 | 10 | Vehicle control | — | po, QD x16 |
| 2 | 8 | Compound P-001 | 10 | po, QD x16 |
| 3 | 8 | Compound Z | 10 | po, QD x16 |

Note:
*= n equals the number of animals
**= Dosing volume: adjust dosing volume based on mouse body weight (5 μL/g).

Tumor measurements and the endpoints: The major endpoint was to see if the tumor growth could be delayed or regressed. Tumor size was measured twice a week in two dimensions using a caliper, and the volume was expressed in mm$^3$ using the formula: V=0.5a×b$^2$ where a and b are the long and short diameters of the tumor, respectively. The tumor size was then used for calculation of tumor growth inhibition (TGI, in percent). The TGI value is an indication of antitumor effectiveness: TGI=(1−T/C)×100%. T and C are the means of relative tumor volumes of the treated and control groups, respectively. T and C are calculated using the formula: T=$T_d/T_0$×100%, C=$C_d/C_0$×100%, where $T_d$ and $C_d$ are tumor volumes of the treated and control animals, respectively, on Day 28 after tumor inoculation; $T_0$ and $C_0$ are tumor volumes of the treated and control animals, respectively, at the start of the treatment The tumor volumes in different groups at different time points are shown in Table 4 and Table 5 and FIG. 1.

Compound P-001 alone demonstrated a strong antitumor activity with a mean tumor size of 99.2 mm$^3$ (Table 4) and TGI=112% (Table 5) while Compound Z produced a moderate antitumor activity with the mean tumor sizes were 141.5 mm$^3$ (Table 4) and TGI=92% (Table 5).

TABLE 4

| | Average Tumor Volume (mm$^3$) | | | | | |
|---|---|---|---|---|---|---|
| Group | Day 0 | Day 4 | Day 6 | Day 8 | Day 11 | Day 13 |
| Vehicle | 124.3 | 173.7 | 214.8 | 240.6 | 282.3 | 336.5 |
| Compound Z | 124.0 | 119.8 | 124.0 | 120.6 | 106.8 | 141.5 |
| Compound P-001 | 124.7 | 94.5 | 91.5 | 90.0 | 96.9 | 99.2 |

TABLE 5

| Group | Treatment | Tumor Size (Day 27, mm$^3$) | TGI (%) |
|---|---|---|---|
| 1 | Vehicle Control | 336.5 ± 48.4 | — |
| 2 | Compound Z (10 mg/kg) | 141.5 ± 16.3 | 92 |
| 3 | Compound P-001 (10 mg/kg) | 99.2 ± 13.5 | 112 |

Thus, Compound Z produced moderate antitumor activity, while Compound P-001 demonstrated strong therapeutic efficacy. Test articles were tolerated well by the tumor-bearing animals.

Example 5

Toxicity Profile Comparison Between Compound P-001 and Compound Z

The promonocytic cell line, Ba/F3, depends on the addition of IL-3 for growth in cell culture. However Ba/F3 cells engineered to express a full length oncogene is capable of rendering Ba/F3 cells factor-independent, but become apoptotic when the oncogene or downstream signaling is inhibited by the addition of small molecule inhibitors. When injected into the tail veins of nude mice, the factor-independent Ba/F3 cells home to the spleen and proliferate to cause a marked splenomegaly. The in vivo proliferation of the factor-independent Ba/F3 cells and appearance of splenomegaly are directly dependent on the activity of the Ba/F3 cells and can be blocked by oral administration of compounds that are effective inhibitors of cell growth. Therefore, this animal model can be used to ascertain the effective doses for Ba/F3 cell inhibition, evaluation of both PK/PD effects as well as a readout of toxicity or MTD.

Table 6 provides a summary of the experimental design.

TABLE 6

| DAY | Ba/F3 cells scaled up in culture (six T-150's) |
|---|---|
| 1 | Cells washed and prepared for injections at $5 \times 10^7$ cells/mL |
| 2 | Inject tail veins of 24 mice (Groups 2-7), 0.1 mL ($5 \times 10^6$ cells) per 1 mouse. No injection for Group 1 (Naïve). |
| 2-8 | Wait 6 days while spleens are growing |
| 8 | Treat vehicle and Compound Z or Compound P-001 by oral gavage. Groups 2-7 QD. |
| 15 | Administer last dose and collect blood for PK analysis according to PK section below. |
| 15 | Weigh animals. Sac mice. Measure spleen and liver weights. |

Figure 2:
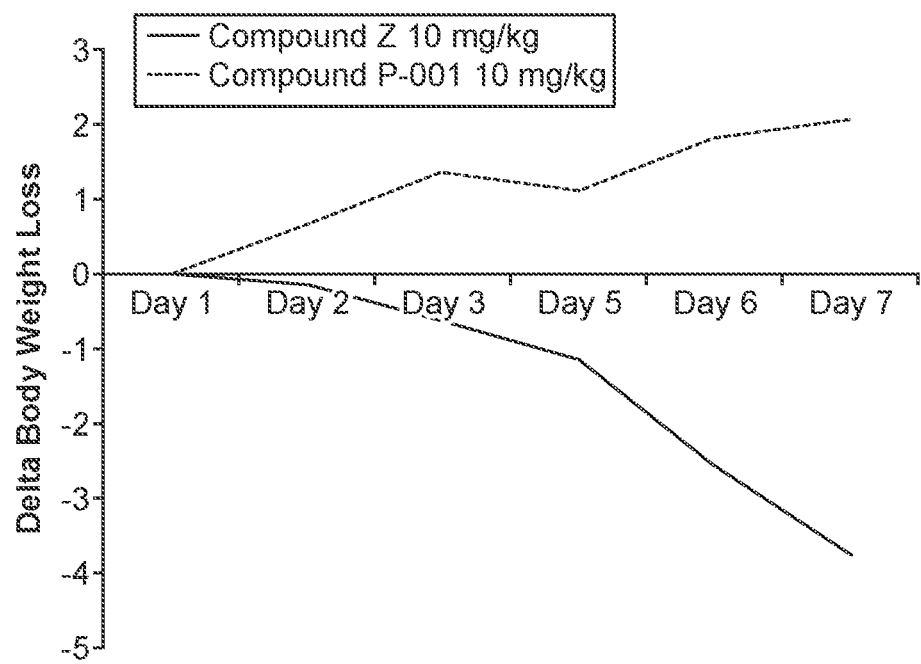
FIG. 2 illustrates the observed toxicity when dosing Compound P-001 and Compound Z at 10 mg/kg to nu/nu mice over a period of 7 days. The Delta Body Weight measurement over time measurement shown by the bottom line represents Compound Z. The Delta Body Weight measurement over time measurement shown by the top line represents Compound P-001.

FIG. 2 illustrates the observed toxicity when dosing Compound P-001 and Compound Z at 10 mg/kg to nu/nu mice over a period of 7 days. Table 7 contains delta body weight changes during period of dosing.

TABLE 7

| | Delta Body Weight Loss | | | | | |
|---|---|---|---|---|---|---|
| Compound | Day 1 | Day 2 | Day 3 | Day 5 | Day 6 | Day 7 |
| Compound Z 10 mg/kg | 0 | −0.125 | −0.6 | −1.125 | −2.475 | −3.75 |
| Compound P-001 10 mg/kg | 0 | 0.75 | 1.375 | 1.125 | 1.825 | 2.075 |

Thus, Compound P-001 shows a significantly improved toxicity profile than Compound Z. As can be seen above, no toxicity was observed for Compound P-001 over the duration of dosing tested in this pharmacology model. Compound Z shows significant toxicity after the $2^{nd}$ day of dosing, and mice continue to deteriorate for remainder of study.

Example 6

Compound Properties

While the inhibitory activity of the compounds on any bromodomain and mutants thereof is important to their activity in treating of disease, the compounds described herein show favorable properties that provide advantages as a pharmaceutical as well.

The compounds described herein are useful for treating disorders related to bromodomain proteins and mutants thereof.

Alphascreen Binding Assay

Binding of compounds of Formula (I) with bromodomain 2, 3, and 4 was assessed using Alphascreen binding assay. The inhibition of the interaction between bromodomain and its acetylated target protein (Filippakopoulos P et al. 2012) was measured quantitatively using recombinant BRD proteins, an acetylated Histone 4 peptide and AlphaScreen™ technology. In absence of inhibition the BRD protein bound to AlphaScreen™ nickel chelate acceptor beads can interact with the acetylated Histone 4 peptide which is immobilized by the AlphaScreen™ Streptavidin coated beads. This interaction brings donor and acceptor beads in proximity. The close proximity allows the singlet oxygen produced by laser excitation of the donor beads to reach the acceptor beads and generate a luminescence signal. BRD inhibitors result in a decrease in the proximity signal through an inhibition of the BRD—acetylated peptide interaction.

Recombinant human bromodomains containing the N-terminal bromodomain (BRD2-BD1 (71-194), BRD3-BD1 (24-144) and BRD4-BD1 (44-164)) or dual bromodomains (BRD4-BD12 (1-477), BRD4-BD12 (1-472)) were prepared and purified as described in protein expression and purification session. The peptide is human Histone $H4_{1-21}K5_{Ac}K8_{Ac}K12_{Ac}K16_{Ac}$-Biotin (Anaspec CA, USA).

Protocol for BRD2, BRD3 and BRD4 assay: All components are prepared in buffer composed of 50 mM HEPES pH 7.5, 100 mM NaCl, 0.01% BSA, 0.01% Triton X-100, 2 mM DTT. 7 μL of Bromodomain protein and 7 μL of peptide are added to wells containing 1 μL of various concentrations of test compounds of Formula (I) or DMSO vehicle in an Alphaplate (PerkinElmer GA, USA) and incubated for 1 hour at room temperature. 4 μL donor and acceptor bead mixture is then added with final concentrations of 7.5 μg/mL. 30 minutes after bead addition, Alpha signal is read on the Envision spectrometer ($\lambda_{Ex}$ 680 nm, $\lambda_{Em}$ 520-620 nm). Final concentrations of bromodomain proteins and peptide are as shown below.

| Assay name | BRD protein (nM) | Peptide (nM) |
|---|---|---|
| BRD2-BD1 | 6 | 41 |
| BRD3-BD1 | 4 | 41 |
| BRD4-BD1 | 6 | 41 |
| BRD2-BD12 | 1 | 10 |
| BRD4-BD12 | 3.7 | 37 |

All data was normalized to the mean of 16 high and 16 low control wells on each plate. A four parameter curve fit of the following formula was then applied:

$$Y=a+(b-a)/(1+(x/c)^d)$$

Where 'a' is the minimum, 'b' is the maximum, 'c' is the $pIC_{50}$ and 'd' is the Hill slope.

Protein Expression and Purification

Recombinant human bromodomains containing the N-terminal bromodomain (BRD2-BD1 (71-194), BRD3-BD1 (24-144) and BRD4-BD1 (44-164)) or dual bromodomains (BRD4-BD12 (1-477), BRD4-BD12 (1-472)) were expressed in *E. coli* cells (in a modified pET vector) with an N-terminal six-His tag and purified using a combination of both IMAC (Ni-affinity) and size exclusion chromatography steps.

Recombinant BRD proteins were expressed using the *E. coli* strain BL21-CodonPlus (DE3) (Agilent Technologies CA, USA). Cells were grown in Terrific Broth (TB) media to an OD600 of 1.2 at 37° C. at which temperature was reduced to 25° C., protein was induced with 1.0 mM isopropyl-ß-D-thiogalactopyranoside ("IPTG") for 12-18 hours and harvested by centrifugation at 8000×g for 20 minutes. Cells were re-suspended in 0.1 M $K_2PO_4$ pH 8.0, 250 mM NaCl, 10% Glycerol, 0.75% NP-40, 25 mM Imidazole, 5 mM beta-mercaptoethanol ("BME") with 0.2 mg/mL Lysosyme, 2.0 mM phenylmethanesulfonyl fluoride ("PMSF"), 25 μg/mL DNAse I, incubated on ice for 30 minutes and lyzed with a cell disruptor (MicroFluidics MA, USA). The lysate was clarified by centrifugation at 20,000×g for 2 hours. The protein was captured with Ni-NTA resin (Life Technologies, USA). Contaminating proteins were washed off with 25 mM Tris-HCl pH 8.3, 250 mM NaCl, 12% Glycerol and 50 mM Imidazole. Following 3× wash steps, protein was eluted step wise using a 50 mM HEPES pH 7.5, 500 mM NaCl and 400 mM Imidazole. The protein was further purified using Gel Filtration column 26/600 Superdex 200 (GE Biosciences NJ, USA) in 50 mM HEPES pH 7.5, 250 mM NaCl. The protein was aliquoted and flash-frozen in liquid Nitrogen.

Oncology Cell Growth Assay

Published bromodomain inhibitors JQ1 and iBET 151 have shown activity in variety of cancer cells such leukemia and lymphoma, multiple myeloma cells, NUT midline carcinoma and glioblastoma cells (Dawson M A et al. 2011; Delmore J E 2011; Chen Z et al. 2013; Filippakopoulos P et al. 2010; Mertz J A et al. 2011; Ott C J et al. 2012). In this study, we test compounds in different cancer cell lines. MV-4-11 and MOLM-13 are AML cell lines harboring a MLL-AF4 and MLL-AF9 translocation, respectively. MM.1S is a multiple myeloma cell line. SK-N-AS, IMR-32 and SK-N-BE(2) are neuroblastoma cell lines. IMR-32 and SK-N-BE(2) cell lines harbor MYCN amplifications.

MV-4-11, MM.1S, IMR-32, SK-N-AS and SK-N-BE(2) were obtained from ATCC (IL, USA) and MOLM-13 were purchased from DSMZ(Braunschweig, German). Cells are cultured as recommended by their sources. For growth inhibition studies 3000 cells are seeded in wells of a 96-well plate in 75 µL of culture media. After several hours, growth media containing compounds of Formula (I) are added to the wells. Compound at a maximal concentration of 5 mM was serially diluted 1:3 for a total of 8 point titration with DMSO as a control. A 1 µL aliquot of each dilution point is added to 249 µL growth media and 75 µL is added to each well containing cells, providing 10 µM compound at the maximum concentration point. The final concentration of DMSO in all wells is 0.2%. Cells are incubated for 72 hours, and 25 µL of CellTiter Glo Reagent (Promega GA, USA) is added to each well. Plates are shaken for approximately 10 minutes and chemiluminescent signal is read on Tecan microplate reader. The measured luminescence correlates directly with cell number.

All data is normalized to the mean of eight DMSO high control wells on each plate. A four parameter curve fit of the following formula was then applied:

$$Y=a+(b-a)/(1+(x/c)^d)$$

Where 'a' is the minimum, 'b' is the maximum, 'c' is the pIC50 and 'd' is the Hill slope.

These data demonstrate that the bromodomain inhibitors tested in the above assays inhibit cell growth in oncology cell lines.

Myc Reporter Assay

In MV-4-11 cells, BRD2, BRD3 and BRD4 bind to the promoter region of MYC and regulate its transcription (Dawson M A et al. 2011). The literature bromodomain inhibitor iBET 151 could disrupt BRD4 recruitment to the MYC promoter and subsequently downregulate c-myc transcription (Dawson M A et al. 2011). Myc protein is a transcription factor that heterodimerizes with an obligatory partner Max and regulates the transcription of genes important for cell proliferation, differentiation, and apoptosis.

This Myc reporter assay is used to monitor the inhibitory effect of compound of Formula (I) on Myc dependent gene expression. Effective compounds could have potential therapeutic effects in Myc-driven tumors.

The MV-4-11 Myc reporter cell line is established by infecting MV-4-11 with VSV-g pseudotyped lentivirus expressing the firefly luciferase gene under the control of a minimal (m) CMV promoter and tandem repeats of the E-box tranonriptional response element (TRE) (Qiagen IL, USA) and selecting cells in 2.5 µg/mL Puromycin.

The MV-4-11 Myc reporter cell line is maintained in Iscove's Modified Dulbecco's Medium containing 10% FBS, 1% PenStep and 2.5 µg/mL Puromycin. Cells are incubated at 37° C. in a humidified atmosphere with 5% $CO_2$. 25,000 cells are seeded in 96-well plate in 50 µL of culture media. After several hours, growth media containing 2X compounds are added to the wells. Compound at a maximal concentration of 5 mM is serially diluted 1:3 for a total of 8 point titration. A 1 µL aliquot of each dilution point is added to 249 µL growth media and 50 µL is added to each well containing cells, providing 10 µM compound at the maximum concentration point. DMSO treated cells serve as a high control and 10 µM JQ1 treated cells serve as a low control. Cells are incubated for a further 24 hours and 25 µL of CellTiter-Fluo Reagent (Promega GA, USA) is added to each well. Plates are shaken for approximately 2 minutes and incubated at 37° C. for 0.5 hour. Fluorescence signal is read in a Tecan Plate reader λex=400 nm, λem=505 nm). 25 µL of One-Glo Reagent (Promega GA, USA) is then added to the plates. Chemiluminescent signal is read on Tecan plate reader. Values from the wells with no cells are subtracted from all samples for background correction. The background corrected fluorescence correlates directly with cell number, and luminescence correlates directly with Myc reporter activity.

All data is normalized to the mean of 8 high control and 4 low control wells on each plate. A four parameter curve fit of the following formula was then applied:

$$Y=a+(b-a)/(1+(x/c)^d)$$

Where 'a' is the minimum, 'b' is the maximum, 'c' is the pIC50 and 'd' is the Hill slope.

It is understood that the results of these assays may vary as assay conditions are varied. Inhibition levels determined under the conditions described herein represent a relative activity for the compounds tested under the specific conditions employed. The cell based assays are likely to show variability due to the complexity of the system and the sensitivity thereof to any changes in the assay conditions. As such, some level of inhibition in the cell based assays is indicative of the compounds having some inhibitory activity for those cells, whereas lack of inhibition below the threshold of the highest concentration tested does not necessarily indicate that the compound has no inhibitory activity on the cells, only that under the conditions tested, no inhibition is observed. In some instances, the compounds were not tested in all of the assays, or assay results were not valid.

All patents, patent applications and other references cited in the specification are indicative of the level of skill of those skilled in the art to which the present disclosure pertains, and are incorporated by reference in their entireties, including any tables and figures, to the same extent as if each reference had been incorporated by reference in its entirety individually. The information provided is intended solely to assist the understanding of the reader. None of the information provided nor references cited is admitted to be prior art to the present disclosure. Each of the references cited is incorporated herein in its entirety and for any purpose.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the present disclosure. Changes therein and other uses will occur to those skilled in the art, which are encompassed within the spirit of the present disclosure, are defined by the scope of the claims.

While this disclosure has been made with reference to specific embodiments, it is apparent that other embodiments and variations of the present disclosure may be devised by others skilled in the art without departing from the true spirit and scope of the present disclosure.

In addition, where features or aspects of the present disclosure are described in terms of Markush groups or other grouping of alternatives, those skilled in the art will recognize that the present disclosure is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the present disclosure.

What is claimed is:

1. A method for treating myelofibrosis comprising administering to a subject in need thereof an effective amount of a compound of Formula (I):

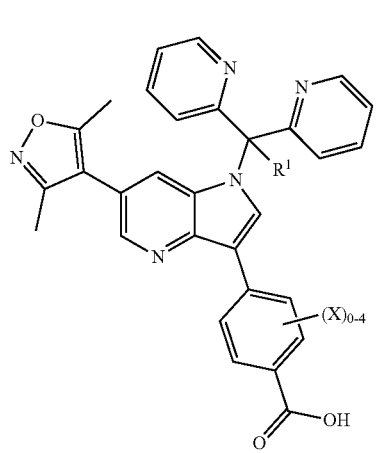

(I)

or a pharmaceutically acceptable salt, a tautomer, a stereoisomer or a deuterated analog thereof, wherein:

R¹ is cyano, halo, or (C₁-C₃)alkyl optionally substituted with 1 to 3 substituents independently selected from the group consisting of halo, methyl, ethyl, methoxy and ethoxy; and X, when present, is halo.

2. The method of claim 1, wherein R¹ is (C₁-C₂)alkyl, cyano or fluoro.

3. The method of claim 2, wherein R¹ is methyl.

4. The method of claim 2, wherein R¹ is fluoro.

5. The method of claim 2, wherein R¹ is cyano.

6. The method of claim 1, wherein the compound of Formula (I) is a compound of Formula (II):

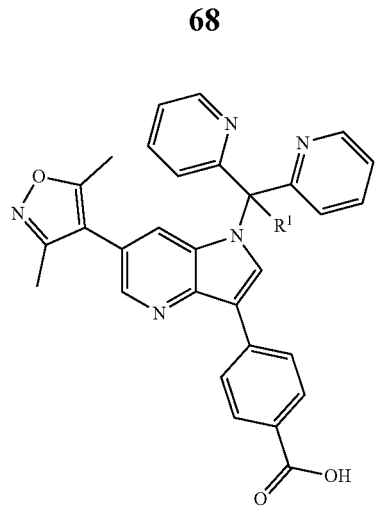

(II)

or a pharmaceutically acceptable salt, a tautomer, a stereoisomer, or a deuterated analog thereof, wherein:

R¹ is (C₁-C₃)alkyl optionally substituted with 1 to 3 substituents independently selected from the group consisting of halo, methyl, ethyl, methoxy and ethoxy.

7. The method of claim 6, wherein R¹ is methyl.

8. The method of claim 1, wherein the compound of Formula (I) is a compound of formula:

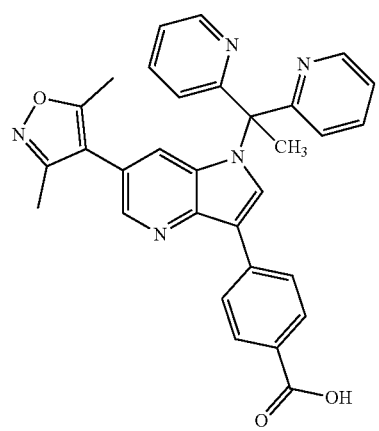 [SMILES: Cc1noc(C)c1-c1cnc2c(-c3ccc(C(=O)O)cc3)cn(C(C)(c3ccccn3)c3ccccn3)c2c1]

or a pharmaceutically acceptable salt, a tautomer, or a deuterated analog thereof.

9. The method of claim 1, further comprising administering one or more additional therapeutic agents.

10. The method of claim 9, wherein the one or more additional therapeutic agents is one or more of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor; xii) a targeted signal transduction inhibitor selected from bortezomib, geldanamycin, and rapamycin; xiii) a biological response modifier selected from imiquimod, interferon-a and interleukin-2; xiv) an IDO inhibitor; xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor, and an aromatase inhibitor (anastrozole letrozole exemestane); xvi) a MEK inhibitor; xvii) a tyrosine kinase inhibitor; xviii) a c-Kit mutant inhibitor, xix) an EGFR inhibitor; or xx) an epigenetic modulator.

11. The method of claim 10, wherein the one or more additional therapeutic agents is an epigenetic modulator selected from the group consisting of:
(a) a DNA methyltransferase;
(b) a histone or protein methyltransferase;
(c) a histone demethylase;
(d) a histone deacetylase inhibitor;
(e) histone acetyltransferase; and
(f) a chromatin remodeler.

12. The method of claim 10, wherein the epigenetic modulator is a histone deacetylase inhibitor selected from the group consisting of: vorinostat, romidepsin, chidamide, panobinostat, belinostat, valproic acid, mocetinostat, abexinostat, entinostat, resminostat, givinostat, and quisinostat.

13. The method of claim 9, wherein the one or more additional therapeutic agents is a kinase inhibitor.

14. The method of claim 8, further comprising administering one or more additional therapeutic agents.

15. The method of claim 14, wherein the one or more additional therapeutic agents is a kinase inhibitor.

16. A method for treating myelofibrosis comprising administering to a subject in need thereof an effective amount of a compound of formula:

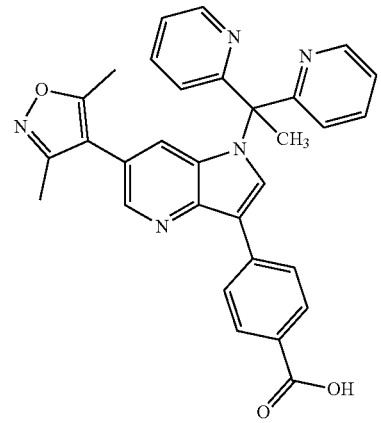 [SMILES: Cc1noc(C)c1-c1cnc2c(-c3ccc(C(=O)O)cc3)cn(C(C)(c3ccccn3)c3ccccn3)c2c1]

or a pharmaceutically acceptable salt thereof, in combination with a kinase inhibitor.

* * * * *